United States Patent
Bellinzoni et al.

(10) Patent No.: US 10,940,196 B2
(45) Date of Patent: Mar. 9, 2021

(54) UNIVERSAL VACCINE FOR VIRAL DISEASES

(71) Applicants: BIOGÉNESIS BAGÓ URUGUAY S.A., Montevideo (UY); BIOGÉNESIS BAGÓ HONG KONG LIMITED, Hong Kong (CN)

(72) Inventors: Rodolfo César Bellinzoni, Tigre (AR); Emmanuel Gérard Etienne Régulier, Vicente López (AR); Ana Romo, Chascomús (AR)

(73) Assignee: BIOGENESIS BAGÓ HONG-KONG LIMITED, Hong Kong (CN)

( * ) Notice: Subject to any disclaimer, the term of this patent is extended or adjusted under 35 U.S.C. 154(b) by 0 days.

(21) Appl. No.: 16/092,660

(22) PCT Filed: Apr. 7, 2017

(86) PCT No.: PCT/IB2017/052030
§ 371 (c)(1),
(2) Date: Oct. 10, 2018

(87) PCT Pub. No.: WO2017/178945
PCT Pub. Date: Oct. 19, 2017

(65) Prior Publication Data
US 2019/0142926 A1    May 16, 2019

Related U.S. Application Data

(60) Provisional application No. 62/320,852, filed on Apr. 11, 2016.

(51) Int. Cl.
| | | |
|---|---|---|
| *A61K 39/135* | (2006.01) | |
| *C07K 14/09* | (2006.01) | |
| *C12N 15/62* | (2006.01) | |
| *A61P 31/14* | (2006.01) | |
| *C07K 14/005* | (2006.01) | |
| *A61K 39/12* | (2006.01) | |
| *A61K 39/00* | (2006.01) | |

(52) U.S. Cl.
CPC ............ *A61K 39/135* (2013.01); *A61K 39/12* (2013.01); *A61P 31/14* (2018.01); *C07K 14/005* (2013.01); *C12N 15/62* (2013.01); *A61K 2039/53* (2013.01); *C07K 2319/00* (2013.01); *C12N 2770/32122* (2013.01); *C12N 2770/32134* (2013.01)

(58) Field of Classification Search
CPC .......... A61K 2039/552; A61K 2039/70; A61K 2039/5258; A61K 2039/55555; A61K 49/0002; A61K 2039/53; A61K 2039/55505; A61K 2039/55511; A61K 2039/55516; A61K 2039/55583; A61K 2039/575; A61K 2039/6087; A61K 39/00; A61P 31/12; A61P 31/20; A61P 31/14; C12N 2760/16061; C12N 2760/16121; C12N 9/506; C12N 2310/3513; C07K 16/10; C07K 2319/00; C07K 14/09
See application file for complete search history.

(56) References Cited

FOREIGN PATENT DOCUMENTS

| | | |
|---|---|---|
| CN | 102168088 B | 12/2012 |
| CN | 105056227 | 11/2015 |
| WO | 2002078732 A1 | 10/2002 |
| WO | 2005/121330 A2 | 12/2005 |
| WO | 2011054011 | 5/2011 |
| WO | 2014150150 | 9/2014 |
| WO | 2014/191903 A1 | 12/2014 |

OTHER PUBLICATIONS

Kianmehr et al. (Medical Microbiology and Immunology; 2015, vol. 204, Iss. 2, 205-213.*
Crisci et al. Vaccine, 2012, vol. 30, pp. 2427-2437.*
Wang et al. Vaccine 2002, pp. 2603-2610.*
Pan et al. Vaccine published on Dec. 2015 on line, vol. 34, Issue 4, pp. 578-585.*

(Continued)

*Primary Examiner* — Bao Q Li
(74) *Attorney, Agent, or Firm* — Law Offices of Albert Wai-Kit Chan, PLLC

(57) ABSTRACT

The present invention relates to a pharmaceutical combination for inducing one or more immune responses and/or for enhancing effectiveness of vaccination in the host, which is capable of inducing cross-protection against multiples strains and/or serotypes of a virus. In one embodiment, the pharmaceutical combination is able to generate protection in food producing animals, such as cattle, sheep, goats, swine and other cloven-hoofed animals with fewer vaccination campaigns. This universal vaccine comprises an inactivated virus with one or more of the following components: polynucleotides encoding viral peptides, polypeptides or proteins in different types of plasmids; viral peptides, polypeptides and proteins; synthetic viral peptides and polypeptides; recombinant viral peptides, polypeptides and proteins; virus-like-particles; virus-like-particles derived from other viruses; proteins used as a carrier or as molecular adjuvant fused to peptides, polypeptides and/or proteins derived from viruses; adjuvants; emulsifiers, molecular adjuvants and carrier systems.

12 Claims, 8 Drawing Sheets
Specification includes a Sequence Listing.

(56) References Cited

OTHER PUBLICATIONS

Antrobus et al. (Molecular Therapy; Milwaukee vol. 22, Iss. 1, (Jan. 2014): 233-238. DOI:10.1038/mt.2013.162. published on line by Aug. 6, 2013).*

Jul. 20, 2017 Written Opinion of the International Searching Authority for PCT/IB2017/052030, Filed Apr. 7, 2017.

Mar. 25, 2020 Extended European Search Report for App. No. EP17782018.0.

Berinstein A et al: "Avridine and LPS from Brucella ovis: Effect on the memory induced by foot-and-mouth disease virus vaccination in mice", Vaccine, Elsevier, Amsterdam, NL, vol. 11, No. 13, Oct. 1, 1993 (Oct. 1, 1993), pp. 1295-1301.

Blanco et. al., Peptide vaccines against foot-and-mouth disease virus, in book: Foot and mouth disease virus: current research and emerging trends, 2017, p. 320.

Cartwright B et al., Serological and Immunological Relationships between the 146S and 12S Particles of Foot-and-Mouth Disease Virus, J. Gen. Virol. (1980), 50, 369-375.

Cartwright et. al, Nature of the Antibody Response to the Foot-and-Mouth Disease Virus Particle, its 12S Protein Subunit and the Isolated Immunizing Polypeptide VP1, J. gen. Virol. (1982),63, 375-38.

Council of Europe, European Pharmacopoeia, 2008, Foot and mouth disease (ruminants) vaccine (inactivated) monograph 0063 Ph. Eur. Suppl. 6.0 Strasbourg, France.

Doel TR et al., Comparative Immunogenicity of 146S, 75S and 12S Particles of Foot-and-Mouth Disease Virus, Archives of Virology 73, 185-191 (1982).

World Reference Laboratory for Foot and Mouth Disease, Quaterly Report, Jan. to Mar. 2017, p. 5.

Laing et al: "The 'Co-Delivery' Approach to Liposomal Vaccines: Application to the Development of influenza-A and hepatitis-B Vaccine Candidates", Journal of Liposome Research., vol. 16, No. 3, Jan. 9, 200 (Jan. 9, 2006), pp. 229-235.

Laplagne D A et al: "Engineering of a polymeric bacteria protein as a scaffold for the multiple display of peptides", Proteins: Structure, Function, and Bioinformatics, John Wiley & Sons, Inc, US, vol. 57, No. 4, Aug. 18, 2004, pp. 820-828.

Matthion et. al., Reintroduction of foot-and-mouth disease in Argentina: characterisation of the isolates and development of tools for the control and eradication of the disease,Vaccine 22 (2004) 4149-4162.

Nagendrakumar et. al., Evaluation of cross-protection between O1 Manisa and O1 Campos in cattle vaccinated with foot-and-mouth disease virus vaccine incorporating different payloads of inactivated O1 Manisa antigen, Vaccine. Feb. 24, 2011;29(10):1906-12.

Rodriguez et. al., A synthetic peptide containing the consensus sequence of the G-H loop region of foot-and-mouth disease virus type-O VP1 and a promiscuous T-helper epitope induces peptide-specific antibodies but fails to protect cattle against viral challenge, Vaccine 21 (2003) 3751-3756.

Sciutto E et al: "*Brucella* spp. lumazine synthase: a novel antigen delivery system", Vaccine, vol. 23, No. 21, Apr. 15, 2005, pp. 2784-2790.

Sobrino et. al.,Foot-and-mouth disease virus: a long known virus, but a current threat, Vet. Res. 32 (2001) 1-30.

Taboga et. al., A Large-Scale Evaluation of Peptide Vaccines against Foot-and-Mouth Disease: Lack of Solid Protection in Cattle and Isolation of Escape Mutants, Journal of Virology, Apr. 1997, p. 2606-2614.

Zakhartchouk A N et al: "Augmentation of immune responses to SARS coronavirus by a combination of DNA and whole killed virus vaccines", Vaccine, vol. 23, No. 35, Aug. 15, 2005 (Aug. 15, 2005), pp. 4385-4391.

Dec. 18, 2020 EP Communication pursuant to Article 94(3) EPC, Application No. EP 17782018.0.

Bucafusco et al. (2015) Foot-and-mouth disease vaccination induces cross-reactive IFN-γ responses in cattle that are dependent on lhe integrity of the 140S particles. Virology. 476: 11-18.

* cited by examiner

Figure 1

| GROUP | IMMUNIZATION STRATEGY | VACCINE | ANIMAL NUMBER | Anti-O1 Campos antibodies titer by ELISA (log10) | | | |
|---|---|---|---|---|---|---|---|
| | | | | 30 DPV | 60 DPV | 90 DPV | 105 DPV |
| 1 | BLS-I$_{(DNA)}$ (0 DPV)/ BLS-I (30 DPV) | D / E | 2072 | 1.10 | 1.19 | 1.17 | 1.10 |
| | | | 2073 | 1.10 | 1.63 | 1.63 | 1.57 |
| | | | 2074 | 1.10 | 1.17 | 1.10 | 1.10 |
| | | | 2075 | 1.10 | 1.62 | 1.79 | Dead by natural causes |
| | | | Mean | 1.10 | 1.40 | 1.42 | 1.26 |
| | | | SD | 0.00 | 0.26 | 0.34 | 0.27 |
| 2 | BLS-I$_{(DNA)}$ (0 DPV)/ BLS-D+BLS-A1+ BLS-I (30 DPV) | D / F | 2076 | 1.10 | 1.10 | 1.10 | 1.10 |
| | | | 2077 | 1.10 | 1.56 | 2.07 | 2.23 |
| | | | 2078 | 1.10 | 1.36 | 1.18 | 1.10 |
| | | | 2079 | 1.10 | 1.30 | 1.52 | 1.63 |
| | | | Mean | 1.10 | 1.33 | 1.47 | 1.51 |
| | | | SD | 0.00 | 0.19 | 0.44 | 0.54 |
| 3 | BLS-I (0 DPV)/ BLS-I (30 DPV) | E / E | 2080 | 1.66 | 2.07 | 1.84 | 1.69 |
| | | | 2081 | 1.43 | 1.85 | 2.17 | 2.21 |
| | | | 2082 | 1.46 | 1.53 | 1.37 | 1.17 |
| | | | 2083 | 1.51 | 1.91 | 1.87 | 2.00 |
| | | | Mean | 1.51 | 1.84 | 1.81 | 1.81 |
| | | | SD | 0.10 | 0.23 | 0.33 | 0.45 |
| 4 | BLS-D+BLS-A1+ BLS-I (0 DPV) / BLS-D+BLS-A1+ BLS-I (30 DPV) | F / F | 2084 | 1.48 | 2.03 | 1.85 | 1.67 |
| | | | 2085 | 1.53 | 1.54 | 1.81 | 1.88 |
| | | | 2086 | 1.26 | 1.63 | 1.40 | 1.18 |
| | | | 2087 | 1.27 | 1.24 | 1.10 | 1.10 |
| | | | Mean | 1.38 | 1.58 | 1.49 | 1.46 |
| | | | SD | 0.14 | 0.34 | 0.31 | 0.38 |
| 5 | Non-vaccinated control | | 026 145 | 0.90 | 0.90 | 0.90 | - |
| | | | 025 887 | 0.90 | 0.90 | 0.90 | - |
| | | | Mean | 0.90 | 0.90 | 0.90 | - |
| | | | SD | 0 | 0 | 0 | - |
| 6 | Inactivated Tetravalent Virus Vaccine: O1 Campos, A2001, C3 Indaial A24 Cruzeiro (Positive Control) (0 DPV) | G | 4703 | 2.78 | 3.57 | 3.60 | 3.90 |
| | | | 4704 | 3.59 | 3.98 | 3.60 | 3.63 |
| | | | 4710 | 2.59 | 2.92 | 2.90 | 2.82 |
| | | | 4711 | 2.96 | 3.52 | 3.60 | 3.40 |
| | | | Mean | 2.98 | 3.50 | 3.42 | 3.44 |
| | | | SD | 0.43 | 0.44 | 0.35 | 0.46 |

Figure 2

Serology against FMD virus O1 Campos strain (60 DPV)

Figure 3

| GROUP | IMMUNIZATION STRATEGY | VACCINE | ANIMAL NUMBER | LESIONS | | | | | PPG (Protection against podal generalization) |
|---|---|---|---|---|---|---|---|---|---|
| | | | | T | RFM | LFM | RHM | LHM | |
| 1 | BLS-I (DNA) (0 DPV)/ BLS-I (30 DPV) | D / E | 2072 | + | + | + | + | + | 0/3 |
| | | | 2073 | + | + | + | + | + | |
| | | | 2074 | + | + | + | + | + | |
| | | | 2075 | Dead by natural causes | | | | | |
| 2 | BLS-I (DNA) (0 DPV)/ BLS-D + BLS-A1 + BLS-I (30 DPV) | D / F | 2076 | + | + | + | + | + | 0/4 |
| | | | 2077 | + | + | + | + | + | |
| | | | 2078 | + | + | + | + | + | |
| | | | 2079 | + | + | + | + | + | |
| 3 | BLS-I (0 DPV)/ BLS-I (30 DPV) | E / E | 2080 | + | + | + | + | + | 0/4 |
| | | | 2081 | + | + | + | + | + | |
| | | | 2082 | + | + | + | + | + | |
| | | | 2083 | + | + | + | + | + | |
| 4 | BLS-D + BLS-A1 + BLS-I (0 DPV) / BLS-D + BLS-A1 + BLS-I (30 DPV) | F / F | 2084 | + | + | + | + | + | 0/4 |
| | | | 2085 | + | + | + | + | + | |
| | | | 2086 | + | + | + | + | + | |
| | | | 2087 | + | + | + | + | + | |
| 5 | Non-vaccinated control | | 025 887 | + | - | - | + | - | 0/2 |
| | | | 026 145 | + | + | + | + | + | |
| 6 | Inactivated Tetravalent Virus Vaccine: O1C, A2001, C3I, A24C (Positive Control) (0 DPV) | G | 4703 | - | - | - | - | - | 4/4 |
| | | | 4704 | - | - | - | - | - | |
| | | | 4710 | + | - | - | - | - | |
| | | | 4711 | + | - | - | - | - | |

Figure 4

| GROUP | IMMUNIZATION STRATEGY | VACCINE | ANIMAL NUMBER | Anti-O1 Campos antibodies titer by ELISA (log10) | |
|---|---|---|---|---|---|
| | | | | 29 DPV | 58 DPV |
| 1 | BLS-I + A2001 Inactivated Virus Vaccine (0 DPV) | A+B | 25 | 2.26 | 2.50 |
| | | | 31 | 2.35 | 2.06 |
| | | | 34 | 1.99 | 1.93 |
| | | | 35 | 2.29 | 2.45 |
| | | | 36 | 2.47 | 3.35 |
| | | | 44 | 2.34 | 2.09 |
| | | | Mean | 2.28 | 2.40 |
| | | | SD | 0.15 | 0.47 |
| 2 | A2001 Inactivated Virus Vaccine (0 DPV) (Negative Control) | B | 28 | 1.33 | 1.39 |
| | | | 32 | 1.20 | 1.35 |
| | | | 40 | 1.19 | 1.63 |
| | | | 47 | 1.30 | 1.39 |
| | | | 60 | 1.23 | 1.42 |
| | | | 64 | 1.32 | 1.41 |
| | | | Mean | 1.26 | 1.43 |
| | | | SD | 0.06 | 0.10 |
| 3 | O1 Campos Inactivated Virus Vaccine (0 DPV) (Positive Control) | C | 30 | 3.15 | 2.91 |
| | | | 33 | 2.99 | 3.60 |
| | | | 39 | 2.93 | 2.48 |
| | | | 51 | 3.60 | 3.45 |
| | | | 61 | 3.44 | 3.39 |
| | | | 63 | 3.17 | 2.44 |
| | | | 65 | 3.30 | 3.11 |
| | | | 66 | 3.38 | 3.38 |
| | | | 69 | 3.54 | 3.09 |
| | | | Mean | 3.28 | 3.09 |
| | | | SD | 0.23 | 0.42 |
| 4 | Non-vaccinated control | | 54 | 0.92 | 0.98 |
| | | | 68 | 0.90 | 0.99 |
| | | | Mean | 0.91 | 0.99 |
| | | | SD | 0.01 | 0.01 |

Figure 6

| GROUP | IMMUNIZATION STRATEGY | VACCINE | ANIMAL NUMBER | Anti-A2001 antibodies titer by ELISA (log10) | |
| --- | --- | --- | --- | --- | --- |
| | | | | 63 DPV | 98 DPV |
| 1 | BLS-I_A2001 + Inactivated O1 Campos Virus Vaccine (0 DPV) / BLS-I_A2001 (28 DPV) | H + J / H | 8096 | 2.33 | 2.20 |
| | | | 8097 | 2.23 | 1.85 |
| | | | 8098 | 2.37 | 2.78 |
| | | | 8099 | 3.48 | 3.25 |
| | | | 8100 | 1.58 | 2.66 |
| | | | 8101 | 2.28 | 2.25 |
| | | | 8102 | 2.78 | 2.82 |
| | | | 8103 | 2.10 | 2.27 |
| | | | 8104 | 2.99 | 2.68 |
| | | | 8105 | 3.60 | 3.55 |
| | | | 8106 | 1.77 | 2.02 |
| | | | 8107 | 2.30 | 2.25 |
| | | | Mean | 2.48 | 2.55 |
| | | | SD | 0.62 | 0.50 |
| 2 | Inactivated A2001 Virus Vaccine (0 DPV) (Positive Control) | I | 8072 | 1.85 | 2.60 |
| | | | 8073 | 3.54 | 3.25 |
| | | | 8074 | 1.99 | 2.29 |
| | | | 8075 | 3.54 | 3.56 |
| | | | 8076 | 3.39 | 3.48 |
| | | | 8077 | 2.49 | 2.25 |
| | | | 8078 | 1.94 | 2.14 |
| | | | 8079 | 3.32 | 4.77 |
| | | | 8080 | 2.29 | 2.44 |
| | | | 8081 | 2.22 | 2.49 |
| | | | 8082 | 1.43 | 1.37 |
| | | | 8083 | 2.86 | 2.88 |
| | | | Mean | 2.57 | 2.80 |
| | | | SD | 0.74 | 0.87 |
| 3 | Inactivated O1 Campos Virus Vaccine (0 PDV) (Negative Control) | J | 8084 | 3.17 | 2.66 |
| | | | 8085 | 1.32 | 1.11 |
| | | | 8086 | 1.63 | 1.87 |
| | | | 8087 | 1.22 | 1.35 |
| | | | 8088 | 1.22 | 1.24 |
| | | | 8089 | 2.06 | 2.09 |
| | | | 8090 | 1.24 | 1.28 |
| | | | 8091 | 1.17 | 1.10 |
| | | | 8092 | 1.84 | 1.81 |
| | | | 8093 | 1.92 | 2.07 |
| | | | 8094 | 1.70 | 1.75 |
| | | | 8095 | 1.51 | 1.73 |
| | | | Mean | 1.67 | 1.67 |
| | | | SD | 0.56 | 0.47 |
| 4 | Non vaccinated | | 2791 | 0.90 | 0.90 |
| | | | 2832 | 0.90 | 0.90 |
| | | | Mean | 0.90 | 0.90 |
| | | | SD | 0 | 0 |

Figure 8

| GROUP | IMMUNIZATION STRATEGY | VACCINE | ANIMAL NUMBER | LESIONS | | | | | PPG (Protection against podal generalization) |
|---|---|---|---|---|---|---|---|---|---|
| | | | | T | RFM | LFM | RHM | LHM | |
| 1 | BLS-I_A2001 + Inactivated O1 Campos Virus Vaccine (0 DPV) / BLS-I_A2001 (28 DPV) | H+J / H | 8096 | + | + | + | + | + | 7/12 |
| | | | 8097 | - | - | - | - | - | |
| | | | 8098 | + | - | - | - | - | |
| | | | 8099 | + | + | + | + | + | |
| | | | 8100 | + | + | - | + | + | |
| | | | 8101 | + | - | - | - | - | |
| | | | 8102 | - | - | - | - | - | |
| | | | 8103 | + | - | + | - | - | |
| | | | 8104 | - | - | - | - | - | |
| | | | 8105 | + | - | + | + | - | |
| | | | 8106 | - | - | - | - | - | |
| | | | 8107 | - | - | - | - | - | |
| 2 | Inactivated A2001 Virus Vaccine (0 DPV) (Positive Control) | I | 8072 | + | - | - | - | - | 12/12 |
| | | | 8073 | + | - | - | - | - | |
| | | | 8074 | + | - | - | - | - | |
| | | | 8075 | - | - | - | - | - | |
| | | | 8076 | - | - | - | - | - | |
| | | | 8077 | - | - | - | - | - | |
| | | | 8078 | + | - | - | - | - | |
| | | | 8079 | - | - | - | - | - | |
| | | | 8080 | + | - | - | - | - | |
| | | | 8081 | - | - | - | - | - | |
| | | | 8082 | + | - | - | - | - | |
| | | | 8083 | - | - | - | - | - | |
| 3 | Inactivated O1 Campos Virus Vaccine (0 DPV) (Negative Control) | J | 8084 | + | + | + | + | + | 0/6 |
| | | | 8085 | Not challenged | | | | | |
| | | | 8086 | + | + | + | + | + | |
| | | | 8087 | Not challenged | | | | | |
| | | | 8088 | Not challenged | | | | | |
| | | | 8089 | + | + | + | + | + | |
| | | | 8090 | Not challenged | | | | | |
| | | | 8091 | Not challenged | | | | | |
| | | | 8092 | + | + | + | + | + | |
| | | | 8093 | + | + | + | + | + | |
| | | | 8094 | + | + | + | + | + | |
| | | | 8095 | Not challenged | | | | | |
| 4 | Non vaccinated | | 2791 | + | + | + | + | + | 0/2 |
| | | | 2832 | + | + | + | + | + | |

Figure 9

Protection against Podal Generalization (PPG)

| Vaccine | Animals Protected % |
|---|---|
| H + J / H | 58 |
| I | 100 |
| J | 0 |
| Non vaccinated | 0 |

Figure 10

| GROUP | IMMUNIZATION STRATEGY | VACCINE | ANIMAL NUMBER | Anti-A2001 antibodies titer by ELISA (log10) 31 DPV | Anti-A2001 antibodies titer by ELISA (log10) 63 DPV |
|---|---|---|---|---|---|
| 1 | BLS-I_A2001 + Inactivated O1 Campos Virus Vaccine (0 DPV) | K | 766 | 1.93 | 2.34 |
| | | | 767 | 1.10 | 1.24 |
| | | | 768 | 2.50 | 3.46 |
| | | | 775 | 2.58 | 3.39 |
| | | | 792 | 1.48 | 1.72 |
| | | | 796 | 1.31 | 1.39 |
| | | | 800 | 1.47 | 2.78 |
| | | | 803 | 1.84 | 2.31 |
| | | | 805 | 2.25 | 2.87 |
| | | | 808 | 1.27 | 2.21 |
| | | | Mean | 1.77 | 2.43 |
| | | | SD | 0.53 | 0.79 |
| 2 | Inactivated A2001 Virus Vaccine (0 DPV) (Positive Control) | L | 771 | 2.04 | 2.20 |
| | | | 772 | 2.05 | 2.91 |
| | | | 793 | 2.18 | 2.29 |
| | | | 807 | 1.99 | 2.30 |
| | | | 809 | 1.94 | 2.67 |
| | | | Mean | 2.04 | 2.47 |
| | | | SD | 0.09 | 0.30 |
| 3 | Inactivated O1 Campos Virus Vaccine (0 DPV) (Negative Control) | M | 763 | 1.10 | 1.40 |
| | | | 784 | 1.23 | 1.28 |
| | | | 788 | 1.10 | 1.21 |
| | | | 794 | 1.21 | 1.51 |
| | | | 802 | 1.22 | 1.19 |
| | | | Mean | 1.17 | 1.32 |
| | | | SD | 0.06 | 0.13 |
| 4 | Non vaccinated | | 770 | 0.90 | 0.90 |
| | | | 779 | 0.90 | 0.90 |
| | | | 806 | 0.90 | 0.90 |
| | | | Mean | 0.90 | 0.90 |
| | | | SD | 0 | 0 |

SEQUENCE LISTING

<160> NUMBER OF SEQ ID NOS: 60

<210> SEQ ID NO 1
<211> LENGTH: 12
<212> TYPE: PRT
<213> ORGANISM: Foot-and-mouth disease virus

<400> SEQUENCE: 1

Thr Thr Thr Thr Gly Glu Ser Ala Asp Pro Val Thr
1               5                   10

<210> SEQ ID NO 2
<211> LENGTH: 10
<212> TYPE: PRT
<213> ORGANISM: Foot-and-mouth disease virus

<400> SEQUENCE: 2

Thr Gly Glu Ser Ala Asp Pro Val Thr Thr
1               5                   10

<210> SEQ ID NO 3
<211> LENGTH: 13
<212> TYPE: PRT
<213> ORGANISM: Foot-and-mouth disease virus

<400> SEQUENCE: 3

Asn Tyr Gly Gly Glu Thr Gln Thr Ala Arg Arg Leu His
1               5                   10

<210> SEQ ID NO 4
<211> LENGTH: 20
<212> TYPE: PRT
<213> ORGANISM: Foot-and-mouth disease virus

<400> SEQUENCE: 4

Glu Thr Gln Ile Gln Arg Arg Gln His Thr Asp Val Ser Phe Ile Met
1               5                   10                  15

Asp Arg Phe Val
            20

<210> SEQ ID NO 5
<211> LENGTH: 17
<212> TYPE: PRT
<213> ORGANISM: Foot-and-mouth disease virus

<400> SEQUENCE: 5

Gln Arg Arg Gln His Thr Asp Val Ser Phe Ile Met Asp Arg Phe Val
1               5                   10                  15

Lys

<210> SEQ ID NO 6
<211> LENGTH: 9
<212> TYPE: PRT
<213> ORGANISM: Foot-and-mouth disease virus

<400> SEQUENCE: 6

Arg Arg Gln His Thr Asp Val Ser Phe
1               5

<210> SEQ ID NO 7
<211> LENGTH: 15
<212> TYPE: PRT
<213> ORGANISM: Foot-and-mouth disease virus

```
<400> SEQUENCE: 7

Leu Arg Thr Ala Thr Tyr Tyr Phe Ala Asp Leu Glu Val Ala Val
1               5                   10                  15

<210> SEQ ID NO 8
<211> LENGTH: 10
<212> TYPE: PRT
<213> ORGANISM: Foot-and-mouth disease virus

<400> SEQUENCE: 8

Ala Tyr His Lys Gly Pro Phe Thr Arg Leu
1               5                   10

<210> SEQ ID NO 9
<211> LENGTH: 21
<212> TYPE: PRT
<213> ORGANISM: Foot-and-mouth disease virus

<400> SEQUENCE: 9

Tyr Ser Arg Asn Ala Val Pro Asn Ala Arg Gly Asp Leu Gln Val Leu
1               5                   10                  15

Ala Gln Lys Val Ala
            20

<210> SEQ ID NO 10
<211> LENGTH: 21
<212> TYPE: PRT
<213> ORGANISM: Foot-and-mouth disease virus

<400> SEQUENCE: 10

Tyr Thr Val Ser Gly Leu Ser Arg Arg Gly Asp Leu Gly Ser Leu Ala
1               5                   10                  15

Ala Arg Val Ala Lys
            20

<210> SEQ ID NO 11
<211> LENGTH: 21
<212> TYPE: PRT
<213> ORGANISM: Foot-and-mouth disease virus

<400> SEQUENCE: 11

Tyr Thr Gly Gly Ser Leu Pro Asn Val Arg Gly Asp Leu Gln Val Leu
1               5                   10                  15

Ala Pro Lys Ala Ala
            20

<210> SEQ ID NO 12
<211> LENGTH: 21
<212> TYPE: PRT
<213> ORGANISM: Foot-and-mouth disease virus

<400> SEQUENCE: 12

Tyr Gly Glu Ser Asp Val Thr Asn Val Arg Gly Asp Leu Gln Val Leu
1               5                   10                  15

Ala Gln Lys Ala Ala
            20

<210> SEQ ID NO 13
<211> LENGTH: 21
<212> TYPE: PRT
<213> ORGANISM: Foot-and-mouth disease virus

<400> SEQUENCE: 13
```

-continued

Tyr Gly Glu Asn Asn Val Thr Asn Val Arg Gly Asp Leu Gln Val Leu
1               5                   10                  15

Ala Gln Lys Ala Ala
            20

<210> SEQ ID NO 14
<211> LENGTH: 21
<212> TYPE: PRT
<213> ORGANISM: Foot-and-mouth disease virus

<400> SEQUENCE: 14

Ser Lys Tyr Ser Ala Pro Gln Asn Arg Arg Gly Asp Leu Gly Pro Leu
1               5                   10                  15

Ala Ala Arg Leu Ala
            20

<210> SEQ ID NO 15
<211> LENGTH: 21
<212> TYPE: PRT
<213> ORGANISM: Foot-and-mouth disease virus

<400> SEQUENCE: 15

Ser Lys Tyr Ser Thr Pro Gln Thr Arg Arg Gly Asp Leu Gly Pro Leu
1               5                   10                  15

Ala Ala Arg Leu Ala
            20

<210> SEQ ID NO 16
<211> LENGTH: 21
<212> TYPE: PRT
<213> ORGANISM: Foot-and-mouth disease virus

<400> SEQUENCE: 16

Ala Val Pro Asn Ala Arg Gly Asp Leu Gln Val Leu Ala Gln Lys Val
1               5                   10                  15

Ala Arg Thr Leu Pro
            20

<210> SEQ ID NO 17
<211> LENGTH: 21
<212> TYPE: PRT
<213> ORGANISM: Foot-and-mouth disease virus

<400> SEQUENCE: 17

Ser Leu Pro Asn Val Arg Gly Asp Leu Gln Val Leu Ala Pro Lys Ala
1               5                   10                  15

Ala Arg Pro Leu Pro
            20

<210> SEQ ID NO 18
<211> LENGTH: 16
<212> TYPE: PRT
<213> ORGANISM: Foot-and-mouth disease virus

<400> SEQUENCE: 18

Leu Arg Gly Asp Leu Gln Val Leu Ala Gln Lys Val Ala Arg Thr Leu
1               5                   10                  15

<210> SEQ ID NO 19
<211> LENGTH: 9
<212> TYPE: PRT
<213> ORGANISM: Foot-and-mouth disease virus -continued

<400> SEQUENCE: 19

Arg Thr Leu Pro Thr Ser Phe Asn Tyr
1               5

<210> SEQ ID NO 20
<211> LENGTH: 18
<212> TYPE: PRT
<213> ORGANISM: Foot-and-mouth disease virus

<400> SEQUENCE: 20

Thr Thr Gln Asp Arg Arg Lys Gln Glu Ile Ile Ala Pro Glu Lys Gln
1               5                   10                  15

Thr Leu

<210> SEQ ID NO 21
<211> LENGTH: 13
<212> TYPE: PRT
<213> ORGANISM: Foot-and-mouth disease virus

<400> SEQUENCE: 21

His Lys Gln Lys Ile Val Ala Pro Val Lys Gln Thr Leu
1               5                   10

<210> SEQ ID NO 22
<211> LENGTH: 11
<212> TYPE: PRT
<213> ORGANISM: Foot-and-mouth disease virus

<400> SEQUENCE: 22

Glu Asp Ala Val Ser Gly Pro Asn Thr Ser Gly
1               5                   10

<210> SEQ ID NO 23
<211> LENGTH: 15
<212> TYPE: PRT
<213> ORGANISM: Foot-and-mouth disease virus

<400> SEQUENCE: 23

Pro Phe Gly His Leu Thr Lys Leu Glu Leu Pro Thr Asp His His
1               5                   10                  15

<210> SEQ ID NO 24
<211> LENGTH: 14
<212> TYPE: PRT
<213> ORGANISM: Foot-and-mouth disease virus

<400> SEQUENCE: 24

Tyr Gly Lys Val Ser Asn Pro Pro Arg Thr Ser Phe Pro Gly
1               5                   10

<210> SEQ ID NO 25
<211> LENGTH: 15
<212> TYPE: PRT
<213> ORGANISM: Foot-and-mouth disease virus

<400> SEQUENCE: 25

Asp Val Ser Leu Ala Ala Lys His Met Ser Asn Thr Tyr Leu Ser
1               5                   10                  15

<210> SEQ ID NO 26
<211> LENGTH: 16
<212> TYPE: PRT
<213> ORGANISM: Foot-and-mouth disease virus

<400> SEQUENCE: 26

Ser Ile Ile Asn Asn Tyr Tyr Met Gln Gln Tyr Gln Asn Ser Met Asp
1               5                   10                  15

<210> SEQ ID NO 27
<211> LENGTH: 12
<212> TYPE: PRT
<213> ORGANISM: Foot-and-mouth disease virus

<400> SEQUENCE: 27

Tyr Gln Asn Ser Met Asp Thr Gln Leu Gly Asp Asn
1               5                   10

<210> SEQ ID NO 28
<211> LENGTH: 15
<212> TYPE: PRT
<213> ORGANISM: Foot-and-mouth disease virus

<400> SEQUENCE: 28

Pro Phe Phe Phe Ser Asp Val Arg Ser Asn Phe Ser Lys Leu Val
1               5                   10                  15

<210> SEQ ID NO 29
<211> LENGTH: 14
<212> TYPE: PRT
<213> ORGANISM: Foot-and-mouth disease virus

<400> SEQUENCE: 29

Phe Phe Arg Ser Thr Pro Glu Asp Leu Glu Arg Ala Glu Lys
1               5                   10

<210> SEQ ID NO 30
<211> LENGTH: 15
<212> TYPE: PRT
<213> ORGANISM: Foot-and-mouth disease virus

<400> SEQUENCE: 30

Leu Lys Ala Arg Asp Ile Asn Asp Ile Phe Ala Ile Leu Lys Asn
1               5                   10                  15

<210> SEQ ID NO 31
<211> LENGTH: 14
<212> TYPE: PRT
<213> ORGANISM: Foot-and-mouth disease virus

<400> SEQUENCE: 31

Ser Glu Glu Lys Phe Val Thr Met Thr Asp Leu Val Pro Gly
1               5                   10

<210> SEQ ID NO 32
<211> LENGTH: 15
<212> TYPE: PRT
<213> ORGANISM: Foot-and-mouth disease virus

<400> SEQUENCE: 32

Val Thr Met Thr Asp Leu Val Pro Gly Ile Leu Glu Lys Gln Arg
1               5                   10                  15

<210> SEQ ID NO 33
<211> LENGTH: 15
<212> TYPE: PRT
<213> ORGANISM: Foot-and-mouth disease virus

<400> SEQUENCE: 33

Tyr Phe Leu Ile Glu Lys Gly Gln His Glu Ala Ala Ile Glu Phe
1               5                   10                  15

<210> SEQ ID NO 34
<211> LENGTH: 15
<212> TYPE: PRT
<213> ORGANISM: Foot-and-mouth disease virus

<400> SEQUENCE: 34

Ala Ala Ile Glu Phe Phe Glu Gly Met Val His Asp Ser Ile Lys
1               5                   10                  15

<210> SEQ ID NO 35
<211> LENGTH: 14
<212> TYPE: PRT
<213> ORGANISM: Foot-and-mouth disease virus

<400> SEQUENCE: 35

Glu Arg Thr Leu Pro Gly Gln Lys Ala Cys Asp Asp Val Asn
1               5                   10

<210> SEQ ID NO 36
<211> LENGTH: 14
<212> TYPE: PRT
<213> ORGANISM: Foot-and-mouth disease virus

<400> SEQUENCE: 36

Gly Pro Tyr Ala Gly Pro Leu Glu Thr Gln Lys Pro Leu Lys
1               5                   10

<210> SEQ ID NO 37
<211> LENGTH: 14
<212> TYPE: PRT
<213> ORGANISM: Foot-and-mouth disease virus

<400> SEQUENCE: 37

Pro Leu Glu Arg Gln Lys Pro Leu Lys Val Arg Ala Lys Leu
1               5                   10

<210> SEQ ID NO 38
<211> LENGTH: 14
<212> TYPE: PRT
<213> ORGANISM: Foot-and-mouth disease virus

<400> SEQUENCE: 38

Gly Pro Tyr Ala Gly Pro Met Glu Arg Gln Lys Pro Leu Lys
1               5                   10

<210> SEQ ID NO 39
<211> LENGTH: 14
<212> TYPE: PRT
<213> ORGANISM: Foot-and-mouth disease virus

<400> SEQUENCE: 39

Pro Met Glu Arg Gln Lys Pro Leu Lys Val Lys Ala Lys Ala
1               5                   10

<210> SEQ ID NO 40
<211> LENGTH: 14
<212> TYPE: PRT
<213> ORGANISM: Foot-and-mouth disease virus

<400> SEQUENCE: 40

Gln Lys Pro Leu Lys Val Lys Ala Lys Ala Pro Val Val Lys

-continued

<210> SEQ ID NO 41
<211> LENGTH: 14
<212> TYPE: PRT
<213> ORGANISM: Foot-and-mouth disease virus

<400> SEQUENCE: 41

Pro Val Lys Lys Pro Val Ala Leu Lys Val Lys Ala Lys Asn
1               5                   10

<210> SEQ ID NO 42
<211> LENGTH: 15
<212> TYPE: PRT
<213> ORGANISM: Foot-and-mouth disease virus

<400> SEQUENCE: 42

Asn Ala Asp Val Gly Arg Leu Ile Phe Ser Gly Glu Ala Leu Thr
1               5                   10                  15

<210> SEQ ID NO 43
<211> LENGTH: 15
<212> TYPE: PRT
<213> ORGANISM: Foot-and-mouth disease virus

<400> SEQUENCE: 43

Ala Val Leu Ala Lys Asp Gly Ala Asp Thr Phe Ile Val Gly Thr
1               5                   10                  15

<210> SEQ ID NO 44
<211> LENGTH: 15
<212> TYPE: PRT
<213> ORGANISM: Foot-and-mouth disease virus

<400> SEQUENCE: 44

Met Arg Lys Thr Lys Leu Ala Pro Thr Val Ala His Gly Val Phe
1               5                   10                  15

<210> SEQ ID NO 45
<211> LENGTH: 15
<212> TYPE: PRT
<213> ORGANISM: Foot-and-mouth disease virus

<400> SEQUENCE: 45

Val Leu Asp Glu Val Ile Phe Ser Lys His Lys Gly Asp Thr Lys
1               5                   10                  15

<210> SEQ ID NO 46
<211> LENGTH: 25
<212> TYPE: PRT
<213> ORGANISM: Foot-and-mouth disease virus

<400> SEQUENCE: 46

Thr Ala Asn Ala Pro Leu Ser Ile Tyr Glu Ala Ile Lys Gly Val Asp
1               5                   10                  15

Gly Leu Asp Ala Met Glu Pro Asp Thr
            20                  25

<210> SEQ ID NO 47
<211> LENGTH: 20
<212> TYPE: PRT
<213> ORGANISM: Foot-and-mouth disease virus

<400> SEQUENCE: 47

Val Asp Val Leu Pro Val Glu His Ile Leu Tyr Thr Arg Met Met Ile
1               5                   10                  15

Gly Arg Phe Cys
            20

<210> SEQ ID NO 48
<211> LENGTH: 15
<212> TYPE: PRT
<213> ORGANISM: Foot-and-mouth disease virus

<400> SEQUENCE: 48

Ser Ala Thr Ser Ile Ile Asn Thr Ile Leu Asn Asn Ile Tyr Val
1               5                   10                  15

<210> SEQ ID NO 49
<211> LENGTH: 15
<212> TYPE: PRT
<213> ORGANISM: Foot-and-mouth disease virus

<400> SEQUENCE: 49

Val Glu Leu Asp Thr Tyr Thr Met Ile Ser Tyr Gly Asp Asp Ile
1               5                   10                  15

<210> SEQ ID NO 50
<211> LENGTH: 20
<212> TYPE: PRT
<213> ORGANISM: Foot-and-mouth disease virus

<400> SEQUENCE: 50

Val Val Ala Ser Asp Tyr Asp Leu Asp Phe Glu Ala Leu Lys Pro His
1               5                   10                  15

Phe Lys Ser Leu
            20

<210> SEQ ID NO 51
<211> LENGTH: 15
<212> TYPE: PRT
<213> ORGANISM: Foot-and-mouth disease virus

<400> SEQUENCE: 51

Tyr Asp Leu Asp Phe Glu Ala Leu Lys Pro His Phe Lys Ser Leu
1               5                   10                  15

<210> SEQ ID NO 52
<211> LENGTH: 15
<212> TYPE: PRT
<213> ORGANISM: Foot-and-mouth disease virus

<400> SEQUENCE: 52

Glu Ala Leu Lys Pro His Phe Lys Ser Leu Gly Gln Thr Tyr Thr
1               5                   10                  15

<210> SEQ ID NO 53
<211> LENGTH: 15
<212> TYPE: PRT
<213> ORGANISM: Foot-and-mouth disease virus

<400> SEQUENCE: 53

His Phe Lys Ser Leu Gly Gln Thr Tyr Thr Pro Ala Asp Lys Ser
1               5                   10                  15

<210> SEQ ID NO 54
<211> LENGTH: 20
<212> TYPE: PRT

<213> ORGANISM: Foot-and-mouth disease virus

<400> SEQUENCE: 54

Thr Asp Val Thr Phe Leu Lys Arg His Phe His Met Asp Tyr Gly Thr
1               5                   10                  15

Gly Phe Tyr Lys
            20

<210> SEQ ID NO 55
<211> LENGTH: 15
<212> TYPE: PRT
<213> ORGANISM: Foot-and-mouth disease virus

<400> SEQUENCE: 55

Lys Thr Leu Glu Ala Ile Leu Ser Phe Ala Arg Arg Gly Thr Ile
1               5                   10                  15

<210> SEQ ID NO 56
<211> LENGTH: 528
<212> TYPE: DNA
<213> ORGANISM: Artificial Sequence
<220> FEATURE:
<223> OTHER INFORMATION: Recombinant polynucleotide

<400> SEQUENCE: 56
atgcattaca gcagaaatgc tgtgcccaac gcgagaggtg accttcaggt gttggctcaa      60
aaggtggcag gtagccttaa gacatccttt aaaatcgcat tcattcaggc ccgctggcac     120
gccgacatcg ttgacgaagc gcgcaaaagc tttgtcgccg aactggccgc aaagacgggt     180
ggcagcgtcg aggtagagat attcgacgtg ccgggtgcat atgaaattcc ccttcacgcc     240
aagacattgg ccagaaccgg cgctatgca gccatcgtcg gtgcggcctt cgtgatcgac      300
ggcggcatct atcgtcatga tttcgtggcg acggccgtta tcaacggcat gatgcaggtg     360
cagcttgaaa cggaagtgcc ggtgctgagc gtcgtgctga cgccgcacca tttccatgaa     420
agcaaggagc atcacgactt cttccatgct catttcaagg tgaagggcgt ggaagcggcc     480
catgccgcct tgcagatcgt gagcgagcgc agccgcatcg cgcttgtc                 528

<210> SEQ ID NO 57
<211> LENGTH: 176
<212> TYPE: PRT
<213> ORGANISM: Artificial Sequence
<220> FEATURE:
<223> OTHER INFORMATION: Recombinant polypeptide

<400> SEQUENCE: 57

Met His Tyr Ser Arg Asn Ala Val Pro Asn Ala Arg Gly Asp Leu Gln
1               5                   10                  15

Val Leu Ala Gln Lys Val Ala Gly Ser Leu Lys Thr Ser Phe Lys Ile
            20                  25                  30

Ala Phe Ile Gln Ala Arg Trp His Ala Asp Ile Val Asp Glu Ala Arg
        35                  40                  45

Lys Ser Phe Val Ala Glu Leu Ala Ala Lys Thr Gly Gly Ser Val Glu
    50                  55                  60

Val Glu Ile Phe Asp Val Pro Gly Ala Tyr Glu Ile Pro Leu His Ala
65                  70                  75                  80

Lys Thr Leu Ala Arg Thr Gly Arg Tyr Ala Ala Ile Val Gly Ala Ala
                85                  90                  95

Phe Val Ile Asp Gly Gly Ile Tyr Arg His Asp Phe Val Ala Thr Ala
            100                 105                 110

Val Ile Asn Gly Met Met Gln Val Gln Leu Glu Thr Glu Val Pro Val
            115                 120                 125

Leu Ser Val Val Leu Thr Pro His His Phe His Glu Ser Lys Glu His
        130                 135                 140

His Asp Phe Phe His Ala His Phe Lys Val Lys Gly Val Glu Ala Ala
145                 150                 155                 160

His Ala Ala Leu Gln Ile Val Ser Glu Arg Ser Arg Ile Ala Leu Val
                165                 170                 175

<210> SEQ ID NO 58
<211> LENGTH: 175
<212> TYPE: PRT
<213> ORGANISM: Artificial Sequence
<220> FEATURE:
<223> OTHER INFORMATION: Recombinant polypeptide

<400> SEQUENCE: 58

Met His Glu Thr Gln Ile Gln Arg Arg Gln His Thr Asp Val Ser Phe
1               5                   10                  15

Ile Met Asp Arg Phe Val Gly Ser Leu Lys Thr Ser Phe Lys Ile Ala
            20                  25                  30

Phe Ile Gln Ala Arg Trp His Ala Asp Ile Val Asp Glu Ala Arg Lys
        35                  40                  45

Ser Phe Val Ala Glu Leu Ala Ala Lys Thr Gly Gly Ser Val Glu Val
    50                  55                  60

Glu Ile Phe Asp Val Pro Gly Ala Tyr Glu Ile Pro Leu His Ala Lys
65                  70                  75                  80

Thr Leu Ala Arg Thr Gly Arg Tyr Ala Ala Ile Val Gly Ala Ala Phe
                85                  90                  95

Val Ile Asp Gly Gly Ile Tyr Arg His Asp Phe Val Ala Thr Ala Val
            100                 105                 110

Ile Asn Gly Met Met Gln Val Gln Leu Glu Thr Glu Val Pro Val Leu
        115                 120                 125

Ser Val Val Leu Thr Pro His His Phe His Glu Ser Lys Glu His His
    130                 135                 140

Asp Phe Phe His Ala His Phe Lys Val Lys Gly Val Glu Ala Ala His
145                 150                 155                 160

Ala Ala Leu Gln Ile Val Ser Glu Arg Ser Arg Ile Ala Leu Val
                165                 170                 175

<210> SEQ ID NO 59
<211> LENGTH: 170
<212> TYPE: PRT
<213> ORGANISM: Artificial Sequence
<220> FEATURE:
<223> OTHER INFORMATION: Recombinant polypeptide

<400> SEQUENCE: 59

Met His Ala Ala Ile Glu Phe Phe Glu Gly Met Val His Asp Ser Ile
1               5                   10                  15

Lys Gly Ser Leu Lys Thr Ser Phe Lys Ile Ala Phe Ile Gln Ala Arg
            20                  25                  30

Trp His Ala Asp Ile Val Asp Glu Ala Arg Lys Ser Phe Val Ala Glu
        35                  40                  45

Leu Ala Ala Lys Thr Gly Gly Ser Val Glu Val Glu Ile Phe Asp Val
    50                  55                  60

Pro Gly Ala Tyr Glu Ile Pro Leu His Ala Lys Thr Leu Ala Arg Thr

```
                65                  70                  75                  80
Gly Arg Tyr Ala Ala Ile Val Gly Ala Ala Phe Val Ile Asp Gly Gly
                    85                  90                  95

Ile Tyr Arg His Asp Phe Val Ala Thr Ala Val Ile Asn Gly Met Met
                    100                 105                 110

Gln Val Gln Leu Glu Thr Glu Val Pro Val Leu Ser Val Val Leu Thr
                    115                 120                 125

Pro His His Phe His Glu Ser Lys Glu His His Asp Phe Phe His Ala
                    130                 135                 140

His Phe Lys Val Lys Gly Val Glu Ala Ala His Ala Ala Leu Gln Ile
145                 150                 155                 160

Val Ser Glu Arg Ser Arg Ile Ala Leu Val
                    165                 170

<210> SEQ ID NO 60
<211> LENGTH: 176
<212> TYPE: PRT
<213> ORGANISM: Artificial Sequence
<220> FEATURE:
<223> OTHER INFORMATION: Recombinant polypeptide

<400> SEQUENCE: 60

Met His Tyr Thr Val Ser Gly Leu Ser Arg Arg Gly Asp Leu Gly Ser
1               5                   10                  15

Leu Ala Ala Arg Val Ala Lys Gly Ser Leu Lys Thr Ser Phe Lys Ile
                    20                  25                  30

Ala Phe Ile Gln Ala Arg Trp His Ala Asp Ile Val Asp Glu Ala Arg
                35                  40                  45

Lys Ser Phe Val Ala Glu Leu Ala Ala Lys Thr Gly Gly Ser Val Glu
            50                  55                  60

Val Glu Ile Phe Asp Val Pro Gly Ala Tyr Glu Ile Pro Leu His Ala
65                  70                  75                  80

Lys Thr Leu Ala Arg Thr Gly Arg Tyr Ala Ala Ile Val Gly Ala Ala
                    85                  90                  95

Phe Val Ile Asp Gly Gly Ile Tyr Arg His Asp Phe Val Ala Thr Ala
                    100                 105                 110

Val Ile Asn Gly Met Met Gln Val Gln Leu Glu Thr Glu Val Pro Val
                    115                 120                 125

Leu Ser Val Val Leu Thr Pro His His Phe His Glu Ser Lys Glu His
            130                 135                 140

His Asp Phe Phe His Ala His Phe Lys Val Lys Gly Val Glu Ala Ala
145                 150                 155                 160

His Ala Ala Leu Gln Ile Val Ser Glu Arg Ser Arg Ile Ala Leu Val
                    165                 170                 175
```

UNIVERSAL VACCINE FOR VIRAL DISEASES

CROSS-REFERENCE TO RELATED APPLICATIONS

This application is a National Stage of Int'l App'l No. PCT/IB2017/052030, Filed Apr. 7, 2017, which claims the benefit of U.S. Ser. No. 62/320,852, Filed Apr. 11, 2016. The entire contents of the preceding applications are hereby incorporated by reference into this application.

Throughout this application, various references are referred to and disclosures of these publications in their entireties are hereby incorporated by reference into this application to more fully describe the state of the art to which this invention pertains.

FIELD OF THE INVENTION

The present invention relates generally to the field of vaccine compositions. In one embodiment, there is provided a platform for viral vaccination using a pharmaceutical combination of one or more formulations that is capable of inducing cross-protection against different serotypes and/or strains of one or more viruses.

BACKGROUND OF THE INVENTION

With the global population expanding at its current rate it is crucial to ensure a safe food supply which is both secure and sustainable. The animal health industry is a key player in this challenge and strives to develop advanced solutions in the interests of a safe, secure and sustainable food supply. Animal health products contribute to improving and maintaining the health and welfare of animals in terms of disease prevention, treatment and control.

One of the most important causes of animal diseases is infections by viruses. Some of them are very contagious and can produce devastating economic losses and impact on public health.

Foot and Mouth Disease (FMD) is an acute systemic viral infection that affects food producing animals, such as cattle, sheep, goats, swine and other cloven-hoofed animals. Despite its very low mortality rate, the highly contagious nature of FMD makes it one of the most serious diseases of the livestock industry in terms of productivity losses and economic impact.

FMD is endemic in many parts of the world. The World Organization for Animal Health (OIE) periodically publishes disease distribution and outbreak world maps. The sanitary status granted by the OIE has a profound economic impact in countries with meat trade-dependent economies because of the market restrictions imposed in countries affected by Foot and Mouth Disease Virus (FMDV). Other viruses which can also cause big impacts on livestock productivity include, but not limited to, Bovine Rotavirus which are the causative agent of neonatal diarrhoea in calves. Bovine Herpesviruses 1 and 5 (BoHV-1 or BHV-1 and BoHV-5 or BHV-5) which are the etiologic agents of Infectious Bovine Rhinotracheitis and Bovine Herpetic Encephalitis respectively, Bovine Parainfluenza Virus 3 (PI3 o BPIV-3) and Bovine Respiratory Syncytial Virus (BRSV) which are both associated with the bovine respiratory disease (BRD) complex, Bovine Viral Diarrhoea Virus (BVDV) which, in addition to diarrhea, can cause immunosuppression, abortion, infertility and a fatal complication called mucosal disease, and the Rabies Virus which is the pathogen causative of lethal encephalitis in both animals and human beings.

The FMDV is a non-lipid-enveloped virus featuring an icosahedral geometry of about 25-30 nm in diameter, containing a single-stranded RNA molecule consisting of about 8500 nucleotides. The RNA molecule comprises a single open reading frame (ORF), encoding structural and non-structural proteins. Its proteome is divided into structural and non-structural proteins. There are four structural proteins: VP1, VP2, VP3 and VP4. Of these proteins, VP1 is the most extensively studied protein owing to its significant roles in virus attachment, protective immunity, and serotype specificity (Sabbir Alam. et al. *Antigenic heterogeneity of capsid protein VP1 in foot-and-mouth disease virus (FMDV) serotype Asia*. Advances and applications in Bioinformatics and Chemistry. 2013, 6: 37-46). Moreover, VP1 is the principal protein used to develop new peptide vaccines (WO 1999066954A1 and Peralta A., et al. *VP1 protein of Foot-and-mouth disease virus (FMDV) impairs baculovirus surface display*. Virus Research. 2013, 175(1): 87-90). The non-structural proteins group comprises the proteins: 2A, 2B, 2C, 3A, 3B, 3C and 3D. These proteins have been used to differentiate between infected and vaccinated animals (Rodriguez A., et al. *Immunogenicity of non-structural proteins of foot-and-mouth disease virus: differences between infected and vaccinated swine*. Archives of virology. 1994, 136(1): 123-131).

Different serotypes of FMDV have been described and each serotype is further divided into multiple strains. These serotypes include: A, O, C, Asia, and the South African types SAT-1, 2, and 3, with A, O, and Asia being the most common.

Despite continuous efforts to develop alternative vaccines against FMD that would not require propagation of the pathogen in large scale, current vaccines are based on inactivated whole virus concentrated and purified to reach a critical mass of antigen capable of generating a protective immune response. These vaccines are manufactured in facilities with Biosafety level 4 OIE (BSL4 OIE). It is estimated that between 2.5 and 3 billion doses are produced annually worldwide.

Peptides vaccines are a safe and economical technology compared to traditional vaccines. The disadvantage of this technology is its poor immunogenicity. Several experiments have been performed with this type of vaccines to test their ability to protect animals (Taboga O., et al. *A Large-Scale Evaluation of Peptide Vaccines against Foot-and-Mouth Disease: Lack of Solid Protection in Cattle and Isolation of Escape Mutants*. Journal of Virology. 1997, 71(4): 2606-2614). The published results showed that the protection reached with the peptide vaccine was lower than 50% of protection in all of the challenges tested in the field. In contrast with these results, inactivated virus vaccines (positive control) commonly reach from 90 to 100% of protection. For this reason, the vaccines which are routinely used as part of eradication programs and in emergency contexts are based on inactivated virus.

Another example of peptide vaccine involves the use of dendrimeric peptides. These peptides are composed of: a core of lysine residues, two or more branches of amino acids and T and B epitopes in its N- and C-terminal, respectively. In the beginning, these dendrimeric peptides were used as antimicrobial peptides (Tam J., et al. Antimicrobial dendrimeric peptides. Eur. J. Biochem. 2002, 269: 923-932), but currently they are used as multi-antigenic peptides for animal vaccination. In one patent application (EP2647390A1), the inventors showed that they have developed a dendrimeric peptide that is capable of eliciting a homologous immune response higher than the linear peptide. The disadvantage of these dendrimeric peptides is the necessity to formulate the vaccine with a high quantity of these peptides in order to confer a solid protection against FMDV. This is truly problematic because large-scale manufacture of such vaccine is economically non-viable.

There are other peptide-based strategies being applied to induce solid immunological protection against different diseases. One of these strategies is the *Brucella* Lumazine Synthase (BLS) technology (see EP1776456B1), which features a protein from *Brucella* spp. capable of forming a decamer with molecular adjuvant properties: antigens of interest (for example; peptides) can be fused to its N-amino end in order to promote an immunological response against the targeted antigen. This decameric assembly of the recombinant BLS protein thus enables the display of ten peptides simultaneously. This technology has the same disadvantage as the other peptides vaccines, namely the dose of antigen needed to obtain immunogenic protection is high. Moreover, due to the large size of the BLS protein, the relative quantity of epitopes is very low. Therefore, in order to overcome this problem, it is necessary to formulate the vaccine with a large quantity of BLS-epitopes to reach the necessary epitopes mass to obtain a solid protection.

Different serotypes of FMDV are distributed around the world. Some regions have more than one serotype and several strains which complicate the sanitary situation and hinder even more the eradication of this disease (Paton D., et al. *Options for control of foot-and-mouth disease: knowledge, capability and policy*. Philosophical Transactions of the Royal Society B. 2009, 364: 2657-2667). Due to the great importance of FMD in terms of economic losses, it is crucial to have a vaccine that can provide cross protection against more than one serotype and/or strain of FMDV. Thus, animals of a specific region could have extensive protection with fewer campaigns of vaccination.

A significant difficulty in formulating vaccines for FMDV is the remarkable antigenic diversity that this virus presents, particularly, the VP1 protein which displays high degree of genetic variation (Haydon D., et al. *Characterizing sequence variation in the VP1 capsid proteins of foot and mouth disease virus (serotype 0) with respect to virion structure*. Journal of Molecular Evolution. 1998, 46(4): 465-475). High degree of genetic variation accounts for the lack of cross-protection among serotypes. When animals are vaccinated against or recovered from a virus of one serotype, they are still susceptible to be infected by viruses from the other six serotypes. Moreover, high degree of antigenic variation within a serotype may cause a vaccine which is protective against one strain becomes ineffective against another strain within that same serotype.

There are plenty of publications that showed the lack of protective response afforded by vaccines based on only one specific strain when used against another strain (Mattion N., et al. *Reintroduction of foot-and-mouth disease in Argentina: Characterization of the isolates and development of tools for the control and eradication of the disease*. Vaccine. 2004, 22: 4149-4162 and Maradei E., et al. *Characterization of foot-and-mouth disease virus from outbreaks in Ecuador during 2009-2010 and cross-protection studies with the vaccine strain in use in the region*. Vaccine. 2011, 29: 8230-8240). In Mattion N. et al. 2004, cross reactivity between strains A/Argentina/79 and A/Argentina/87 was compared. The results showed that there was no reactivity between one strain and the monoclonal antibody of the other.

In Maradei E. et al., protection data showed that cattle vaccinated with one dose of monovalent O1/Campos vaccine induced only 6% protection (one animal protected and 15 animals unprotected) against challenge with the virus O Ecuador 46-2010, and 18% (3 animals protected and 13 animals unprotected) for the revaccinated animals. Moreover, experiments with animals vaccinated with O1 Manisa and challenged against O1 Campos demonstrated that only vaccinating with high payloads of O1 Manisa could achieve protection against O1 Campos (Nagendrakumar S. B., et al. *Evaluation of cross-protection between O1 Manisa and O1 Campos in cattle vaccinated with foot-and-mouth disease virus vaccine incorporating different payloads of inactivated O1 Manisa antigen*. Vaccine. 2011, 29(10): 1906-1912).

In order to overcome the lack of cross-protection problem and in view of the wide range of different peptides that currently exist, tailor-made peptides vaccines could help to resolve this issue due to its ability to easily change the vaccine target. Although peptide vaccines seems to be a good strategy to obtain cross-protection, this kind of vaccines is weekly immunogenic and unviable economically. Moreover, they do not elicit a strong cell-mediated immune response that is the cornerstone to achieve a total immunogenic protection (Becker Y., et al. *Need for cellular and humoral immune responses in bovines to ensure protection from foot-and-mouth disease virus (FMDP)—a point of view*. Virus Genes. 1994, 8: 199-214). Indeed, FMDV specific cell-mediated immune response depends on the integrity and stability of the virus capsid antigen; therefore, peptides vaccines are not capable of triggering a solid cell-mediated response. In addition, it has been demonstrated that cell-mediated immune response is of crucial importance for the cross-reactive protection against heterologous strains (Bucafusco D., et al. *Foot-and-mouth disease vaccination induces cross-reactive IFN-γ responses in cattle that are dependent on the integrity of the 140S particles*. Virology. 2015, 476: 11-18). Thus, it is highly recommended to add an inactivated FMDV to the vaccine formulation in order to trigger a stronger humoral and cell-mediated immune responses.

For all the reasons that have been discussed above, it is proposed to combine an inactivated FMD whole virus antigen with other vaccine technologies in order to take advantage of the abilities of the inactivated antigen to induce strong cellular immunological response and in order to use the novel vaccine technologies to achieve broad cross-protection and specificity through the triggering of strong and broad antibody responses. This novel universal vaccine against FMD represents a great tool in the fight against the FMDV pandemics worldwide and will provide a solution to an unmet market and technical need of affording total protection against all serotypes and different strains of FMDV. Among the novel technologies, peptides antigens stand out as excellent candidates for the combination with inactivated antigens because of the multi-target ability of peptides vaccines.

Nowadays it is absolutely essential that GMP standards be strictly followed for the development of manufacturing processes for the production of pharmaceutical and biotechnological products. Compliance with these requirements ensures a high standard of quality and reliability in the product produced.

The present invention, for the first time, introduces a platform for obtaining a wide range of vaccines that meets the GMP requirements. In one embodiment, there is provided a combination of inactivated viruses with at least one of the following components: polynucleotides encoding viral peptides, polypeptides or proteins in different types of plasmids; synthetic viral peptides or polypeptides; recombinant viral peptides, polypeptides or proteins; virus-like-particles; proteins used as a carrier or as molecular adjuvant fused to peptides, polypeptides and/or proteins derived from one or more viruses; adjuvants; emulsifiers, molecular adjuvants and carrier systems. It is expected that the present invention could develop a universal vaccine to protect an animal against one or more viral diseases.

SUMMARY OF THE INVENTION

In one embodiment, the present invention provides a detailed procedure for the formulation of a universal vaccine that is capable of protecting against a wide range of serotypes and/or strains of viruses (including but are not limited to Foot-and-Mouth Disease Virus (FMDV), Bovine Rotavirus, Bovine Herpesviruses 1 and 5 (BoHV-1 or BHV-1 and BoHV-5 or BHV-5). Bovine Parainfluenza Virus 3 (PI3 or BPIV-3), Bovine Respiratory Syncytial Virus (BRSV). Bovine Viral Diarrhoea Virus (BVDV) and Rabies Virus).

In one embodiment, the present invention provides one or more formulations comprising one or more inactivated viruses, including but not limited to FMDV, Bovine Rotavirus. BoHV-1 and BoHV-5. BPIV-3, BRSV, BVDV and Rabies Virus, with different components in different doses. The formulations are composed of whole inactivated viruses with one or more of the following components: polynucleotides encoding viral peptides, polypeptides or proteins in different types of plasmids; synthetic viral peptides or polypeptides; recombinant viral peptides, polypeptides or proteins; virus-like-particles; proteins used as a carrier or as molecular adjuvant fused to peptides, polypeptides and/or proteins derived from viruses; adjuvants; emulsifiers, molecular adjuvants and carrier systems.

In one embodiment, the present invention discloses a vaccine formulation capable of inducing cross-protection against different serotypes or strains of a virus, comprising whole inactivated virus and at least one of the following components: (a) polynucleotides encoding peptides, polypeptides or proteins of the virus: (b) synthetic peptides or polypeptides of the virus: (c) recombinant peptides, polypeptides or proteins of the virus: (d) virus-like-particles of the virus: (e) virus-like-particles derived from other viruses displaying recombinant peptides, polypeptides or proteins of the virus: and (f) peptides, polypeptides or proteins as carriers or molecular adjuvants that are or are not fused to peptides, polypeptides or proteins of the virus. In one embodiment, the virus includes but not limited to FMDV, Bovine Rotavirus, BoHV-1 and BoHV-5, BPIV-3, BRSV, BVDV and Rabies Virus.

In one embodiment, the present invention provides different formulations comprising a whole inactivated FMDV with different components in different doses. The formulations can be composed of whole inactivated FMDV with at least one of the following components: polynucleotides encoding FMDV peptides, polypeptides or proteins in different types of plasmids; synthetic FMDV peptides or polypeptides; recombinant FMDV peptides, polypeptides or proteins; FMD virus-like-particles: virus-like-particles derived from other viruses displaying recombinant FMDV peptides, polypeptides or proteins; proteins used as a carrier or as molecular adjuvant fused to peptides, polypeptides and/or proteins derived from FMDV; adjuvants; emulsifiers, molecular adjuvants and carrier systems.

The present invention also provides a pharmaceutical combination for inducing one or more immune responses towards one or more viral diseases in a host and/or for enhancing effectiveness of vaccination in the host, comprising: (a) one or more vaccine formulations disclosed herein capable of eliciting the immune responses in the host: and (b) one or more molecular adjuvants which enhances the immune responses in the host, wherein the virus vaccines and the molecular adjuvants can be administered separately or together.

The present invention also provides a method of vaccinating a host susceptible to virus infection, comprising administrating to the host the pharmaceutical combination of the present invention to induce an immune response, wherein the vaccine formulation and the molecular adjuvant are administered to the host separately or together.

In one embodiment, the pharmaceutical combination comprising one or more vaccine formulations of the present invention is capable of ensuring a high protection against one or more viruses, such as FMDV, Bovine Rotavirus. BoHV-1 and BoHV-5, BPIV-3, BRSV, BVDV and Rabies Virus, etc., through induction of cell-mediated and humoral components of the immunological response.

In one embodiment, the pharmaceutical combination comprising one or more vaccine formulations of the present invention is capable of ensuring a high protection against FMDV through induction of cell-mediated and humoral components of the immunological response.

In one embodiment, the pharmaceutical combination of the present invention could be administered to cloven-hoofed host such as cattle, sheep, goats or swine, to induce immune response against one or more viruses infection, such as FMDV, Bovine Rotavirus. BoHV-1 and BoHV-5, BPIV-3, BRSV, BVDV and Rabies Virus, etc.

In one embodiment, the pharmaceutical combination comprising one or more vaccine formulations of the present invention has the advantage to generate immunogenic cross-protection with fewer vaccination campaigns.

In one embodiment, the present invention provides a pharmaceutical combination comprising a universal vaccine that complies with GMP standards.

BRIEF DESCRIPTION OF THE FIGURES

FIG. 1 and FIG. 2 show serology results obtained in a clinical trial in bovines that compares different pharmaceutical combinations of vaccine formulations based on BLS carrier protein fused to different FMDV peptide epitopes. The different vaccine formulations tested were combinations of recombinant BLS proteins fused to FMDV peptide epitopes or naked plasmid DNA encoding the different BLS-FMDV epitopes. Experimental vaccines were administered on days 0 and 30 of the study using a prime/boost strategy at 0 and 30 DPV (Day Post Vaccination). Serological responses were assayed at different time post vaccination: 30 DPV, 60 DPV, 90 DPV and 105 DPV. Sequences of BLS-I$_{(DNA)}$ (SEQ ID NO. 56), BLS-D (SEQ ID NO. 58), BLS-A1 (SEQ ID NO. 59), and BLS-I (SEQ ID NO. 57) are shown in Table 2. BLS-I$_{(DNA)}$/BLS-I: pharmaceutical combination of vaccine formulation containing polynucleotide "BLS-I$_{(DNA)}$" (SEQ ID NO. 56) and fusion protein BLS-I (SEQ ID NO. 57); BLS-I$_{(DNA)}$/BLS-D+BLS-A1+BLS-I: pharmaceutical combination of vaccine formulation containing polynucleotide BLS-I$_{(DNA)}$ (SEQ ID NO. 56) and fusion proteins BLS-D (SEQ ID NO. 58). BLS-A1 (SEQ ID NO. 59) and BLS-I (SEQ ID NO. 57); BLS-I/BLS-I: pharmaceutical combination of vaccine formulation containing fusion protein BLS-I (SEQ ID NO. 57) only; BLS-D+BLS-A+BLS-I/BLS-D+BLS-A1+BLS-I: pharmaceutical combination of vaccine formulation containing fusion proteins BLS-D (SEQ ID NO. 58), BLS-A1 (SEQ ID NO. 59) and BLS-I (SEQ ID NO. 57). Vaccine formulations D, E, F and G are described in Table 3 and the vaccination scheme of the animals is shown in Table 4. An inactivated tetravalent virus vaccine (O1 Campos, A2001. C3 Indaial and A24 Cruzeiro) was used as Positive Control (+). A competitive enzyme-linked immunosorbent assay (ELISA) was performed in order to measure the O1 Campos antibody titer present in the serological responses obtained. Antibody titers were expressed as the reciprocal $\log_{10}$ of serum dilutions giving 50% of the absorbance recorded in the control wells (virus without serum).

FIG. 3 shows the results obtained in a challenge assay for the different vaccines and immunization strategy tested. The analysis of the infection results were realized at 7 dpi (day post infection). The different pharmaceutical combinations of vaccine formulations and immunization strategy were the same as that described in FIG. 1. An inactivated tetravalent virus vaccine (O1 Campos, A2001, C3 Indaial and A24 Cruzeiro) was used as Positive Control (+). T: tongue. RFM: right fore member. LFM: left fore member. RHM: right hind member. LHM: left hind member. Symbols "+" refers to the animal that has symptoms of infection by FMDV on that member. Symbols "–" means the animal does not has symptoms of infection by FMDV on that member. The tongue is not taken into account for analysis because it is the inoculation site. Animals were defined as "protected" when their members (RFM, LFM, RHM and LHM) do not show any symptom.

FIG. 4 and FIG. 5 show O1 Campos strain specific serology results obtained in a cross-protection clinical assay in bovines that enabled comparison between different pharmaceutical combinations of vaccine formulations. Experimental vaccines were all administered on day 0. The different pharmaceutical combinations of vaccine formulations tested were: (1) BLS-I (SEQ ID NO. 57) applied in the left side of the animal and inactivated FMDV serotype type A2001 whole virus applied in the right side of the animal (Vaccine Formulations A and B); (2) inactivated FMDV serotype type A2001 whole virus: Negative control (–) (Vaccine Formulation B); (3) inactivated FMDV serotype type O1 Campos whole virus: Positive Control (+) (Vaccine Formulation C); (4) Animals not vaccinated: A competitive enzyme-linked immunosorbent assay (ELISA) was used in order to measure the O1 Campos antibody titer present in the serological responses obtained. Antibody titers in y-axis were expressed as the reciprocal $\log_{10}$ of serum dilutions giving 50% of the absorbance recorded in the control wells (virus without serum). Serological responses were measured at 29 and 58 days post vaccination.

FIG. 6 and FIG. 7 show A2001 strain specific serology results obtained in a clinical trial in bovines that enabled comparison between different pharmaceutical combinations of vaccine formulations. Serological responses were assayed at different times: 63 DPV and 98 DPV. Inactivated O1 Campos Virus Vaccine: whole inactivated O1 Campos virus particles (negative control). Inactivated A2001 Virus Vaccine: whole inactivated A2001 virus particles (positive control). The sequence of BLS-I_A2001 (SEQ ID NO. 60) is shown in Table 2. Group 1 (BLS-I_A2001+Inactivated O1 Campos Virus Vaccine): two different vaccine formulations, the first one containing fusion protein BLS-I_A2001 (SEQ ID NO. 60) and the second one whole inactivated O1 Campos virus particles, that were applied in different sides of the animals. Vaccine formulations H, I and J are described in Table 7. Negative control (–): whole inactivated O1 Campos virus particles. Positive Control (+): whole inactivated A2001 virus particles. Antibody titers were expressed as the reciprocal $\log_{10}$ of serum dilutions giving 50% of the absorbance recorded in the control wells (virus without serum).

FIG. 8 and FIG. 9 show the results obtained in a challenge assay with virulent A2001 FMD virus for the different pharmaceutical combination of vaccine formulations tested. The analysis of the infection results were realized at 7 dpi. Negative control (–): whole inactivated O1 Campos virus particles. Positive Control (+): whole inactivated A2001 virus particles. T: tongue. RFM: right fore member. LFM: left fore member. RHM: right hind member. LHM: left hind member. Symbols "+" refers to the animal that has symptoms of infection by FMDV on that member. Symbols "–" means the animal does not has symptoms of infection by FMDV on that member. The tongue is not taken into account for the analysis because it is the inoculation site. Animals were defined as "protected" when they do not show any symptom in their members (RFM, LFM, RHM and LHM). The values in y-axis were expressed as the percentage of animals protected over the total animals challenged against O1 Campos FMDV.

FIG. 10 and FIG. 11 show A2001 strain specific serology results obtained in a clinical trial in bovines that enabled comparison between different pharmaceutical combinations of vaccine formulations and immunization strategies. Experimental vaccines were all administered on day 0. Serological responses were assayed at different time post vaccination: 31 DPV and 63 DPV. Inactivated O1 Campos Virus Vaccine: whole inactivated O1 Campos virus particles (negative control). Inactivated A2001 Virus Vaccine: whole inactivated A2001 virus particles (positive control). Sequence of BLS-I_A2001 (SEQ ID NO. 60) is shown in Table 2. BLS-I_A2001+Inactivated O1 Campos Virus Vaccine: vaccine formulation containing whole inactivated O1 Campos virus particles and fusion protein BLS-I_A2001 (SEQ ID NO. 60). Vaccine formulations K, L and M are described in Table 10. Negative control (–): whole inactivated O1 Campos virus particles. Positive Control (+): whole inactivated A2001 virus particles. Antibody titers were expressed as the reciprocal $\log_{10}$ of serum dilutions giving 50% of the absorbance recorded in the control wells (virus without serum).

DETAILED DESCRIPTION OF THE INVENTION

Figure 5:
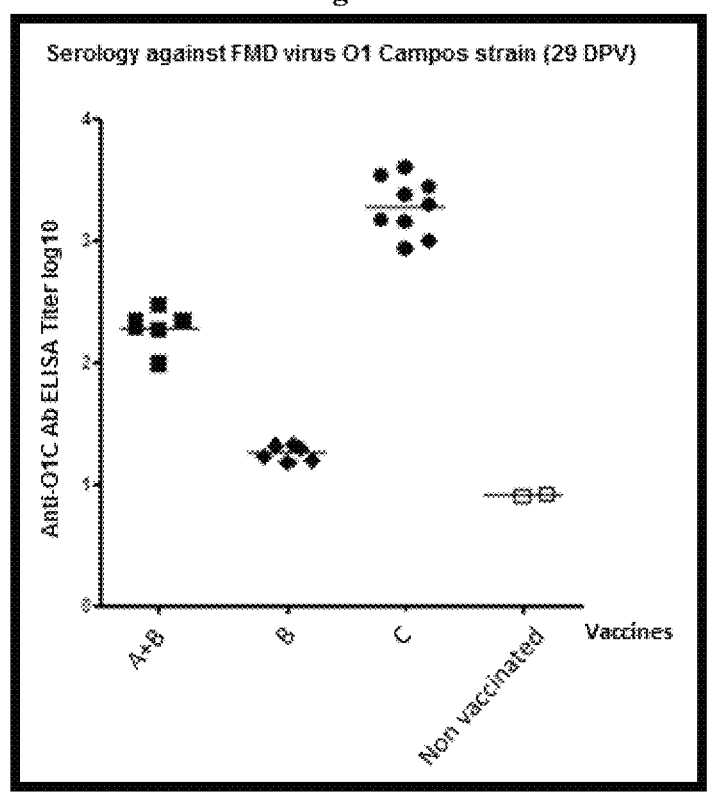

The method described in this patent application illustrates the formulation process to achieve a high quality vaccine for one or more viruses such as FMDV, Bovine Rotavirus, BoHV-1 and BoHV-5, BPIV-3. BRSV, BVDV and Rabies Virus, etc.

In one embodiment, the present invention relates to a method to formulate a universal vaccine against one or more serotypes and/or strains of a virus such as FMDV. Bovine Rotavirus, BoHV-1 and BoHV-5, BPIV-3, BRSV, BVDV and Rabies Virus, etc., in order to obtain cross-protection with only one vaccination.

In one embodiment, the present invention provides immunogenic components to formulate different vaccines in order to ensure cross protection against all or different serotypes or strains of a virus, such as FMDV, Bovine Rotavirus, BoHV-1 and BoHV-5, BPIV-3. BRSV, BVDV and Rabies Virus, etc.

In one embodiment, the present invention provides immunogenic components to formulate different vaccines in order to ensure a total or cross protection against different FMDV serotypes and/or strains. The use of the whole inactivated FMDV in combination with one or more immunogenic components ensures a high protection that comprises cellular and humoral components of the immunological response.

In one embodiment, the universal vaccine of the present invention can specifically induce one or more targeted immune response against all or different serotypes and/or strains of a virus (such as FMDV, Bovine Rotavirus, BoHV-1 and BoHV-5, BPIV-3, BRSV, BVDV and Rabies Virus, etc.) that are present in a specific region.

In one embodiment, the formulations of the present invention comprise inactivated viruses with one or more of the following components: polynucleotides encoding viral peptides, polypeptides or proteins in different types of plasmids; synthetic viral peptides or polypeptides; recombinant viral peptides, polypeptides or proteins; virus-like-particles: virus-like-particles derived from other viruses; proteins used as a carrier or as molecular adjuvant fused to peptides, polypeptides and/or proteins derived from viruses: adjuvants: emulsifiers, molecular adjuvants and carrier systems. The viruses include but are not limited to FMDV. Bovine Rotavirus, BoHV-1 and BoHV-5, BPIV-3, BRSV, BVDV and Rabies Virus.

In one embodiment, the formulations of the present invention comprise whole inactivated FMDV with one or more of the following components: polynucleotides encoding FMDV peptides, polypeptides or proteins in different types of plasmids: synthetic FMDV peptides or polypeptides; recombinant FMDV peptides, polypeptides or proteins; FMD virus-like-particles; virus-like-particles derived from other viruses displaying recombinant FMDV peptides, polypeptides or proteins; proteins used as a carrier or as molecular adjuvant fused to peptides, polypeptides and/or proteins derived from FMDV; adjuvants; emulsifiers, molecular adjuvants and carrier systems.

Polynucleotides Encoding Viral Peptides, Polypeptides or Proteins in Different Types of Plasmids One of ordinary skill in the art would readily recognize that the present invention can be designed using any combination of polynucleotides derived from various viruses, such as FMDV, Bovine Rotavirus, BoHV-1 and BoHV-5, BPIV-3, BRSV, BVDV and Rabies Virus, etc.

The present invention can also be designed using a combination of different polynucleotides of FMDV. In one embodiment, these universal vaccines can comprise one or more polynucleotides that encode entire, partial or variant sequences of FMDV proteins such as capsid proteins VP1, VP2, VP3 and VP4: or non-structural proteins such as 2A, 2B, 2C, 2D, 3A, 3B, 3C and 3D; or any polynucleotide sequences that encode the peptides of SEQ ID NO. 1-55 (Table 1) or the variants, fragments, homologous sequences or functional analogues of such peptides. These polynucleotide sequences can be cloned in any expression vector known in the art that is capable of expressing these sequences in a eukaryotic cell environment. Suitable expression vectors can also be constructed by techniques of recombinant technology generally known in the art. Examples of expression vectors with sequences encoding FMDV epitopes include, but are not limited to, pcDNA3.1/ P1-2A3C3D, plasmid that comprise sequences encoding the viral structural protein precursor P1-2A (VP0, VP1 or VP3) and the non-structural proteins 3C and 3D (Cedillo-Barron L., et al. *Induction of a protective response in swine vaccinated with DNA encoding foot-and-mouth disease virus empty capsid proteins and the 3D polymerase*. Journal of General Virology. 2001, 82: 1713-1724); and the plasmids pCEIM and pCEIS that confer protection against FMDV in mice and swine due to VP1 DNA sequences cloned within them (Wong H T., et al. *Plasmids Encoding Foot-and-Mouth Disease Virus VP1 Epitopes Elicited Immune Responses in Mice and Swine and Protected Swine against Viral Infection*. Virology. 2000, 278: 27-35).

Viral Peptides. Polypeptides and/or Proteins (Recombinant or Synthetic)

One of ordinary skill in the art would readily recognize that the present invention can be designed using a combination of different recombinant or synthetic peptides, polypeptides and/or proteins derived from viruses, such as FMDV. Bovine Rotavirus, BoHV-1 and BoHV-5, BPIV-3, BRSV, BVDV and Rabies Virus, etc.

In one embodiment, the composition of the present invention comprises a combination of different FMDV-derived amino acid sequences. For example, one or more FMDV-derived amino acid sequences would encode the entire, partial or variant sequences of FMDV capsid proteins such as VP1, VP2, VP3 and VP4; or non-structural proteins such as 2A, 2B, 2C, 2D, 3A, 3B, 3C and 3D. In another embodiment, the amino acid sequences can be any of the peptides of SEQ ID NO. 1-55 (Table 1) or the variants, fragments, homologous sequences or functional analogues of those peptides. Examples of suitable polypeptides derived from FMDV include, but are not limited to, one or more native, synthetic or recombinant peptides, polypeptides or proteins constructed entirely, partially or mutated from the G-H loop of FMDV VP1 and a promiscuous artificial Th site derived from measles virus (UBITh1) which could give protection against FMD O1 Taiwan in pigs (Wang C Y., et al. *Effective synthetic peptide vaccine for foot-and-mouth disease in swine*. Vaccine. 2002, 20: 2603-2610); native, synthetic or recombinant peptides, polypeptides and proteins derived entirely, partially or mutated from immunogenic epitopes in the VP1 (129-169), 3A (21-35), and 3D (346-370) proteins of the A/HuBWH/CHA/2009 strain of FMDV that elicits production of virus-neutralizing antibodies against serotype-A in cattle and guinea pigs (Zhang Z., et al. *Efficacy of synthetic peptide candidate vaccines against serotype-A foot-and-mouth disease virus in cattle*. Applied Microbiology and Biotechnology. 2015, 99(3): 1389-1398). In one embodiment, the polypeptides are native, synthetic or recombinant peptides and polypeptides derived entirely, partially or mutated from the hypervariable region of the GH loop, which can vary in length depending on the strain but is usually comprised between amino acids 135 and 160 of the VP1 capsid protein of FMDV. The hypervariable region of the GH loop of the VP1 protein contains major epitopes and is one of the major sites of phylogenetic diversity between FMDV strains since it represents an evasion mechanism from the pressure of the immune system for the diverging strains of FMDV. Indeed, antibodies developed by the host against this hypervariable loop specific of one strain are neutralizing antibodies against this specific strain but will not be neutralizing against another FMDV divergent strain. Therefore, the percentage of homology for different sequences is highly variable. Thus a person skilled in the art can readily understand that the peptides and polypeptides derived from the GH loop and recognized as useful for this invention are functional analogues and can have an amino acids sequence homology as low as 10% with the GH loop peptides of SEQ ID NO. 9-18 (Table 1). In another embodiment, the polypeptides are native, synthetic or recombinant peptides and polypeptides derived entirely, partially or mutated from the hypervariable region of the GH loop of the VP1 capsid protein of FMDV (amino acids 135-160) and that contain the RGD motif (sequence of 3 amino acids:

Arg-Gly-Asp) described as the sequence that binds integrin receptors of the eukaryotic cell upon infection by FMDV (Berinstein A., et al. *Antibodies to the vitronectin receptor (integrin alpha V beta 3) inhibit binding and infection of foot-and-mouth disease virus to cultured cells*. Journal of Virology. 1995, 69(4): 2664-2666).

Virus-Like-Particles (VLP)

One of ordinary skill in the art would readily recognize that the present invention can be designed using one or more virus-like-particles originated from viruses, such as FMDV, Bovine Rotavirus, BoHV-1 and BoHV-5, BPIV-3, BRSV, BVDV and Rabies Virus, etc.

In one embodiment, the present invention can be designed using FMD virus-like-particles. Construction, cloning and expression of FMD virus-like-particles can be accomplished by recombinant technology generally known in the art. In one embodiment, the virus-like-particles are composed entirely of FMDV capsid proteins VP0, VP1 and VP3 that are expressed by recombinant technology and spontaneously assemble into particles without incorporation of the viral genome. In another embodiment, the FMDV capsid proteins are mutated. They are non-replicating and non-infectious vaccine candidates that are capable to mimic the epitope presentation of the native virus. Virus-like-particles technology tested as vaccine candidates for FMDV achieved a potent protective immune responses in guinea pigs, swines and cattle (Guo H-C., et al. *Foot-and-mouth disease virus-like particles produced by a SUMO fusion protein system in Escherichia coli induce potent protective immune responses in guinea pigs, swine and cattle*. Veterinary Research. 2013, 44: 48; and Terhuja M., et al. *Comparative efficacy of virus like particle (VLP) vaccine of foot-and-mouth-disease virus (FMDV) type O adjuvanted with poly I:C or CpG in guinea pigs*. Biologicals. 2015, 43(6): 437-443). Moreover, by including a mutated version of 3C protease in frame with the expression of the polypeptide (P1-2A), the yield of structural proteins was improved and the virus-like-particles obtained proved to be capable of eliciting humoral and cell mediated immune response (Bhat S., et al. *Novel immunogenic baculovirus expressed virus-like particles of foot-and-mouth disease (FMD) virus protect guinea pigs against challenge*. Research in Veterinary Science. 2013, 95(3): 1217-1223).

In another embodiment, the present invention comprises the use of virus-like-particles featuring non-FMDV backbones but enabling the presentation on their surface of FMDV recombinant antigens. As an example of this technology, the "Metavax" platform could be used since it was described previously as a carrier of recombinant immunogenic peptides or large proteins of interest (U.S. Pat. No. 7,678,374). Due to its flexibility and versatility regarding engineering of virus-like-particles forming fusion proteins, Metavax is a suitable technology in order to express FMDV peptides, polypeptides or proteins.

Peptides, Polypeptides and Proteins as Carriers Fused to Peptides, Polypeptides or Proteins with Viral Epitopes In one embodiment, the present invention can be designed with any peptide polypeptide or protein as carriers fused to various epitopes derived from viruses, such as FMDV, Bovine Rotavirus, BoHV-1 and BoHV-5, BPIV-3, BRSV, BVDV and Rabies Virus, etc.

In one embodiment, the present invention can be designed with any peptide, polypeptide or proteins as carriers fused to various FMDV epitopes. The FMDV epitopes could be entire, partial or variant sequences of VP1 protein as disclosed in several publications: amino acid residue 144-159 of serotype O1 Kaufbeuren (O1K) (Pfaff E., et al. *Antibodies against a preselected peptide recognize and neutralize foot and mouth disease virus*. The EMBO Journal. 1982, 1(7): 869-874); amino acid residues 25-41 and 200-213 of serotype O1K (Bittle J., et al. *Protection against foot-and-mouth disease by immunization with a chemically synthesized peptide predicted from the viral nucleotide sequence*. Nature. 1982, 298: 30-33); amino acid residue 66-80 of O/UKG/35/2001 (Gerner W., et al. *Identification of a novel foot-and-mouth disease virus specific T-cell epitope with immunodominant characteristics in cattle with MHC serotype A31*. 2007. Vet. Res. 38: 565-572); amino acid residues 1-12, 17-29 and 194-211 of serotype Asia1 (Zhang Z-W., et al. *Screening and identification of B cell epitopes of structural proteins of foot-and-mouth disease virus serotype Asia1*. Veterinary Microbiology. 2010, 140(1-2): 25-33): amino acid residues 106-115 and 4-13 of strain AF/72 (Liu X-S., et al. *Identification of H-2d Restricted T Cell Epitope of Foot-and-mouth Disease Virus Structural Protein VP1*. Virology Journal. 2011, 8: 426). In one embodiment, the peptide or polypeptides are native, synthetic or recombinant peptides and polypeptides derived entirely, partially or mutated from VP1 FMDV capsid protein. For example, the peptides derived from VP1 FMDV capsid protein are SEQ ID NO. 1-21 as shown in Table 1, as well as their variants or functional analogues. The hypervariable loop of the VP1 protein among amino acid residue 135-160 is one of the major sites of phylogenetic diversity between FMDV strains. Percentages of homology for the hypervariable region of the GH loop of the VP1 protein are highly variable. In another embodiment, the polypeptides are native, synthetic or recombinant peptides and polypeptides derived entirely, partially or mutated from the hypervariable region of the GH loop of the VP1 capsid protein of FMDV and that contain the RGD motif (sequence of 3 amino acids: Arg-Gly-Asp). Furthermore, peptides derived from FMDV epitopes could be entire, partial or variant sequences of other capsid proteins, for example, VP2 (amino acid residue 40-50), VP3 (amino acid residue 26-39) and VP4 (amino acid residue 30-41) of serotype Asia1 (Zhang Z-W., et al. *Screening and identification of B cell epitopes of structural proteins of foot-and-mouth disease virus serotype Asia1*. Veterinary Microbiology. 2010, 140(1-2): 25-33). In addition, the peptides derived from FMDV epitopes could be entire, partial or variant sequences of non-structural proteins (NSP), for example, 2B (PFFFSDVRSNSFKLV (SEQ ID NO.28), FFRSTPEDLERAEK (SEQ ID NO.29)), 2C (LKARDINDIFAILKN (SEQ ID NO.30), SEEKFVTMTDLVPG (SEQ ID NO.31)), 3B (ERTLPGQKACDDVN (SEQ ID NO.35), GPYAGPLETQKPLK (SEQ ID NO.36), PLERQKPLKVRAKL (SEQ ID NO.37), GPYAGPMERQKPLK (SEQ ID NO.38), PMERQKPLKVKAKA (SEQ ID NO.39), QKPLKVKAKAPVVK (SEQ ID NO.40)) from serotype OIK (Hohlich B-J., et al. *Identification of Foot-and-Mouth Disease Virus-Specific Linear B-Cell Epitopes To Differentiate between Infected and Vaccinated Cattle*. Journal of Virology. 2003, August: 8633-8639); protein 3A (amino acid residues 11-25 and 21-35), 3C (amino acid residues 121-135 and 166-180) of strain O1K (Blanco E. et al. *Identification of T-Cell Epitopes in Nonstructural Proteins of Foot-and-Mouth Disease Virus*. Journal of Virology. 2001. April: 3164-3174); and protein 3D (amino acid residues 301-315, 326-340, 346-360, 351-365, 356-370 and 406-420) of strain C-S8 (Gerner W., et al. *Identification of novel foot-and-mouth disease virus specific T-cell epitopes in c/c and d/d haplotype miniature swine*. Virus Research. 2006, 121(2): 223-228).

In another embodiment, examples of peptides with FMDV epitopes are shown in Table 1 (SEQ ID NO. 1-55). The present invention also encompasses peptides that are homologous sequences or functional analogues to the peptides of Table 1. In yet another embodiment, the peptides with FMDV epitopes are native, synthetic or recombinant peptides and polypeptides derived entirely, partially or mutated from the hypervariable region of the GH loop of the VP1 (135-160) region of FMDV capsid protein and that contain the RGD motif (sequence of 3 amino acids: Arg-Gly-Asp).

The peptide, polypeptide or proteins carriers should be able to present the immunogenic epitopes of the FMDV. In one embodiment, these carriers are enhancers of immunogenic response. One example of these carriers could be the swine immunoglobulin G heavy-chain constant region that was fused with a tandem-repeat multiple-epitope gene which contained three copies of each of two immunogens corresponding to amino acid residues 141-160 and 200-213 of VP1 of the FMDV O/China/99 strain (Shao J-J., et al. *Promising Multiple-Epitope Recombinant Vaccine against Foot-and-Mouth Disease Virus Type O in Swine*. Clinical and Vaccine Immunology. 2011, 18(1): 143-149). Another example could be the fusion protein designed with the sequences of VP1 and bovine IFN-γ that proved to be an inducer of humoral and cell-mediated response (Shi X-J., et al. *Expressions of Bovine IFN-γ and Foot-and-Mouth Disease VP1 antigen in P. pastoris and their effects on mouse immune response to FMD antigens*. Vaccine. 2006, 82-89). One of ordinary skill in the art would readily recognize and/or construct peptide or polypeptide carriers suitable for use in the present invention.

Inactivated Viruses

The present invention can be designed using any strains and/or serotypes of inactivated viruses, such as FMDV, Bovine Rotavirus, BoHV-1 and BoHV-5, BPIV-3, BRSV, BVDV and Rabies Virus, etc.

The present invention can also be designed using any type of inactivated FMDV, including but not limited to, the strains O1 Campos, C3 Indaial, A24 Cruzeiro and A2001, or the serotypes of FMDV such as O, A, C, SAT1, SAT2, SAT3 or ASIA1. The vaccines of the present invention can include one or more virus of different strains and/or different serotypes. The strains that can be used in the formulation of the present invention will depend on the predominant strains in the region of intended vaccination. In one embodiment, the strains formulated in the vaccine can be PanAsia strain serotype O which was responsible for an explosive pandemic in Asia and extended to parts of Africa and Europe from 1998 to 2001 (Knowles N., et al. *Pandemic Strain of Foot-and-Mouth Disease Virus Serotype O*. Emerging Infectious Diseases. 2005, 11(12): 1887-1893). Other strains include, but not limited to, O Manisa, O PanAsia-2 (or equivalent), O BFS or Campos, A24 Cruzeiro. Asia 1 Shamir, A Iran-05 (or A TUR 06), A22 Iraq, SAT 2 Saudi Arabia (or equivalent i.e. SAT 2 Eritrea), A Eritrea, SAT 2 Zimbabwe, SAT 1 South Africa, A Malaysia 97 (or Thai equivalent such as A/NPT/TAI/86), A Argentina 2001 (A2001), O Taiwan 97 (pig-adapted strain or Philippine equivalent), A Iran '96, A Iran '99, A Iran 87 or A Saudi Arabia 23/86 (or equivalent), A15 Bangkok related strain, A87 Argentina related strain, C Noville, SAT 2 Kenya. SAT 1 Kenya, SAT 3 Zimbabwe and other strains that could appear in the future according to FAO World Reference Laboratory for Foot-and-Mouth Disease. The inactivation process is generally known in the art; for example, it can be performed by adding chloroform and binary ethylenimine (BEI) two times. Alternatively, the viral particles can be inactivated using a solvent and/or a detergent and/or others proteins denaturants. In yet another embodiment, the viral particles can be inactivated or attenuated by genetic changes in its genome (Rieder E., et al. *Vaccines Prepared from Chimeras of Foot-and-Mouth Disease Virus (FMDV) Induce Neutralizing Antibodies and Protective Immunity to Multiple Serotypes of FMDV*. Journal of Virology. 1994, 68(11): 7092-7098).

Adjuvants, Emulsifiers, Molecular Adjuvants and Carrier Systems

The present invention can be designed using different types of adjuvants, emulsifiers, molecular adjuvants and carrier systems. In one embodiment, the formulation of the present invention includes, but not limited to, aluminium salts, aluminium hydroxide gel, saponine or derivatives, like QS21, lymph cytokines, CpG, poly I:C, toll-like receptors agonists, immune stimulating complexes (ISCOMs), liposomes, incomplete Freund's adjuvant, liposyn, tyrosine stearate, squalene. L121, Emulsigen, monophosphoryl lipid A (MPL), Montanide ISA adjuvants (ISA 15 VG, ISA 25 VG, ISA 28 VG, ISA 35 VG. ISA 201 VG, ISA 206 VG, ISA 207 VG, ISA 50 V2, ISA 50 V4, ISA 61 VG, ISA 70, ISA 71 VG, ISA 71 R VG, ISA 720, ISA 760, ISA 761 VG, ISA 763 A VG, ISA 775, ISA 780), Montanide IMS adjuvants (IMS 251 C. IMS 1312 VG. IMS 1313 VG N, IMS 2215, IMS 3012), Montanide GEL O1, Montanide GEL 02, light mineral oils, metabolisable oils, polysorbate 20, polysorbate 40, polysorbate 60, polysorbate 65, polysorbate 80, polysorbate 85, polysorbate 120, sorbitan monostearate, sorbitan tristearate, sorbitan monolaurate, sorbitan monooleate, sorbitan trioleate, sorbitan monopalmitate and other efficacious adjuvants and emulsifiers. In another embodiment, the vaccine formulation is an emulsion, such as a water-in-oil emulsion (W/O) or an oil-in-water (O/W) emulsion or a water-in-oil-in-water emulsion (W/O/W) or an oil-in-water-in-oil (O/W/O) emulsion. In another embodiment, the vaccine formulation comprises a mix of an emulsion and one or more additional adjuvants. Other examples of carrier systems that could be applied in this vaccine formulation are liposomes that can lead to TH1 or TH2 response (Badiee A., et al. *The role of liposome size on the type of immune response induced in BALB/c mice against leishmaniasis: rgp63 as a model antigen*. Experimental Parasitology. 2011, 132(4): 403-409), microinanospheres, nanoparticles such as poly(lactic-co-glycolic) acid (PLGA) and polysaccharides (Akagi T., et al. *Biodegradable Nanoparticles as Vaccine Adjuvants and Delivery Systems: Regulation of Immune Responses by Nanoparticle-Based Vaccine*. Adv. Polym. Sci. 2012, 247: 31-64), dendrimers (Sheng K-C., et al. *Delivery of antigen using a novel mannosylated dendrimer potentiates immunogenicity in vitro and in vivo*. European Journal of Immunology. 2008, 38(2): 424-436), micellar systems, gold nanoparticles (Dykman L., et al. *Use of a synthetic foot-and-mouth disease virus peptide conjugated to gold nanoparticles for enhancing immunological response*. Gold Bull. 2015, 48: 93-101) and Immune-stimulating complexes (ISCOMs) generally known in the art.

In one embodiment, the universal vaccine of the present invention could be administered by syringe injection, needle free injection, microneedle patch and delivery. The pharmaceutical combination can be administered by different routes such as oral, intramuscular (IM), subcutaneous (SC), intradermal (ID), intranasal spray (INS).

In one embodiment, the pharmaceutical combination of this invention contains antigenic epitopes derived from FMDV capsid protein. The antigenic epitopes may be derived from, for example, A. O and C serotypes; African SAT1, SAT2 and SAT3 serotypes; and Asia 1 serotype. In one embodiment, the antigenic epitope is derived from the FMDV VP1 protein.

Carrier System—Protein or Dendrimeric Peptides as Carriers or Molecular Adjuvant In one embodiment, the vaccine formulations of the present invention utilize protein or dendrimeric peptides as carriers of foreign peptides, polypeptides and/or proteins. In one embodiment, the BLS protein is used as a carrier or as molecular adjuvant in order to redirect the immune response towards a specific strain or serotype. In some embodiments, the N-amino end of BLS protein is fused to a foreign peptide, polypeptides and/or proteins.

In one embodiment, the foreign peptide, polypeptide and/or protein comprise epitopes of viruses such as FMDV, Bovine Rotavirus. BoHV-1 and BoHV-5, BPIV-3, BRSV. BVDV and Rabies Virus, etc. In one embodiment, the BLS is fused to viral peptides, polypeptides or proteins derived entirely, partially or mutated from the capsid proteins VP1, VP2, VP3 and VP4, or non-structural protein of viruses such as FMDV, Bovine Rotavirus, BoHV-1 and BoHV-5. BPIV-3, BRSV, BVDV and Rabies Virus, etc. In one embodiment, the fusion proteins can induce immune response against one or more viruses in host.

In another embodiment, the foreign peptide, polypeptide and/or protein comprises FMDV epitopes. In one embodiment, the foreign peptides, polypeptides and/or proteins are fused to the protein carrier and adjuvant BLS in order to trigger a strong immune response. In one embodiment, the BLS or its variants is fused to FMDV peptides, polypeptides or proteins derived entirely, partially or mutated from the capsid proteins VP1, VP2, VP3 and VP4, or non-structural protein 2A. 2B, 2C, 2D, 3A, 3B, 3C and 3D. In some embodiments, the BLS or its variants is fused to one or more FMDV peptides or their variants or homologs as shown in Table 1 (SEQ ID NO. 1-55). In another embodiment, the BLS or its variants is fused to one or more peptides that are homologous sequences or functional analogues to the peptides of Table 1. In one embodiment, the BLS or its variants is fused to one or more native, synthetic or recombinant peptides and polypeptides derived entirely, partially or mutated from the hypervariable region of the GH loop of the VP1 (135-160) region of FMDV capsid protein and that contain the RGD motif (sequence of 3 amino acids: Arg-Gly-Asp) as described above. In another embodiment, the BLS or its variants protein is fused to proteins, polypeptides and peptides with peptide or polypeptide as the linker. In certain embodiments, the fusion proteins can induce immune response against FMDV in host. In one embodiment, the vaccine formulations further comprises one or more inactivated FMDV. In another embodiment, the vaccine formulations further comprises one or more plasmid DNA. In one embodiment, the plasmid DNA encodes fusion protein of BLS and peptides, polypeptides and/or proteins derived from FMDV. In one embodiment, the BLS or its variants is used as molecular adjuvant without any FMDV peptide, polypeptide and/or protein fused.

In various embodiments, the universal vaccine can be formulated using linear peptides epitopes in tandem. In another embodiment, a combination of T and B epitopes can be used (Blanco E. et al. *Identification of T-Cell Epitopes in Nonstructural Proteins of Foot-and-Mouth Disease Virus*. Journal of Virology. 2001. April: 3164-3174).

In certain embodiments, in the formulation of the universal vaccine, the polypeptides used to present the immunogenic antigens are dendrimeric peptides that could adopt different configurations. For example, dendrimeric peptides can be configured to contain one or more peptides derived from FMDV epitopes (Blanco E., et al. B *Epitope Multiplicity and B/T Epitope Orientation Influence Immunogenicity of Foot-and-Mouth Disease Peptide Vaccines*. Clinical and Developmental Immunology. 2013, Article ID 475960 and Cubillos C. *Enhanced Mucosal Immunoglobulin A Response and Solid Protection against Foot-and-Mouth Disease Virus Challenge Induced by a Novel Dendrimeric Peptide*. Journal of Virology. 2008, July: 7223-7230). Other examples of dendrimeric peptides were described in a recent publication (Monsó M., et al. *Influence of configuration chemistry and B Epitope Orientation on the Immune Response of Branched Peptide Antigens*. Bioconjugate Chemistry: 24(4), 578-585, 2013). The FMDV epitopes presented on the dendrimeric peptides could be copies of the same epitope or different epitopes in order to provide protection against different strains and/or serotypes of FMDV.

In another embodiment, the dendrimeric peptides can be constructed by fusing FMDV immunogenic peptides only.

In one embodiment, the universal vaccine formulation comprises one or more BLS chimeric protein carrying different peptides, polypeptides and/or proteins derived from different FMDV types in order to give protection against different types of FMDV.

In another embodiment, different peptides, polypeptides and/or proteins from FMDV can be fused to the BLS protein in order to give protection against different types of FMDV.

In certain embodiments, one or more peptides, polypeptides and/or proteins from FMDV fused to the BLS protein are derived from B epitopes and/or T epitopes of FMDV.

In one embodiment, the criteria of choosing different peptides, polypeptides and/proteins from FMDV to be fused with BLS depend on the type of FMDV one need protection against. This invention is capable to design vaccines against one specific strain, against different strains of the same serotype or against different serotypes. For protection against one specific strain, a combination of peptides derived from B epitope and T epitope of that strain is recommended in order to reach a high protection levels (Blanco E., et al. B *Epitope Multiplicity and BIT Epitope Orientation Influence Immunogenicity of Foot-and-Mouth Disease Peptide Vaccines*. Clinical and Developmental Immunology: Article ID 475960, 2013). For protection against more than one strain, it is necessary to combine peptides derived from epitopes of different strains (Cao Y., et al. *Evaluation of cross-protection against three topotypes of serotype O foot-and-mouth disease virus in pigs vaccinated with multi-epitope protein vaccine incorporated with poly(I:C)*. Veterinary Microbiology. 2014, 168(2-4): 294-301), preferably peptides derived from both B epitope and T epitope of FMDV. For protection against more than one serotype, it is necessary to combine peptides derived from epitopes of different serotypes, preferably peptides derived from both B epitope and T epitope.

In one embodiment, examples of peptides with FMDV epitopes include, but not limited to, the peptides described in Table 1. One would recognize that the present invention is not limited to the following peptides; the present invention encompasses the following peptides as well as their variants, homologous sequences and/or functional analogues.

TABLE 1

Peptide Sequences From different FMDV Strains

| SEQ ID NO. | Dataset | Sequence | Amino acid residue | Protein region | FMDV strain |
|---|---|---|---|---|---|
| 1 | Peptide_A | TTTTGESADPVT | 1-12 | VP1 | Asia 1 |
| 2 | Peptide_B | TGESADPVTT | 4-13 | VP1 | AF/72 |
| 3 | Peptide_C | NYGGETQTARRLH | 17-29 | VP1 | Asia 1 |
| 4 | Peptide_D | ETQIQRRQHTDVSFIMDRFV | 21-40 | VP1 | O1 Campos |
| 5 | Peptide_E | QRRQHTDVSFIMDRFVK | 25-41 | VP1 | O1 Kaufbeuren |
| 6 | Peptide_F | RRQHTDVSF | 26-34 | VP1 | O/ISA/1/74 |
| 7 | Peptide_G | LRTATYYFADLEVAV | 66-80 | VP1 | O/UKG/35/2001 |
| 8 | Peptide_H | AYHKGPFTRL | 106-115 | VP1 | AF/72 |
| 9 | Peptide_I | YSRNAVPNARGDLQVLAQKVA | 136-156 | VP1 | O1 Campos |
| 10 | Peptide_I_A2001 | YTVSGLSRRGDLGSLAARVAK | 136-156 | VP1 | A2001 |
| 11 | Peptide_I_Jincheon | YTGGSLPNVRGDLQVLAPKAA | 136-156 | VP1 | O/SKR/JC/2014 |
| 12 | Peptide_I_Bhutan | YGESDVTNVRGDLQVLAQKAA | 136-156 | VP1 | BHU/1/2013 |
| 13 | Peptide_I_SAU | YGENNVTNVRGDLQVLAQKAA | 136-156 | VP1 | SAU/3/2013 |
| 14 | Peptide_I_China | SKYSAPQNRRGDLGPLAARLA | 136-156 | VP1 | A/HY/CHA/2013 |
| 15 | Peptide_I_Vietnam | SKYSTPQTRRGDLGPLAARLA | 136-156 | VP1 | A/VN/T11D/2013 |
| 16 | Peptide_J | AVPNARGDLQVLAQKVARTLP | 140-160 | VP1 | O1 Campos |
| 17 | Peptide_J_JinCheon | SLPNVRGDLQVLAPKAARPLP | 140-160 | VP1 | O/SKR/JC/2014 |
| 18 | Peptide_K | LRGDLQVLAQKVARTL | 144-159 | VP1 | O1 Kaufbeuren |
| 19 | Peptide_L | RTLPTSFNY | 157-165 | VP1 | O1 Campos |
| 20 | Peptide_M | ITQDRRKQEIIAPEKQTL | 194-211 | VP1 | Asia 1 |
| 21 | Peptide_N | HKQKIVAPVKQTL | 201-213 | VP1 | O1 Campos |
| 22 | Peptide_O | EDAVSGPNTSG | 40-50 | VP2 | Asia 1 |
| 23 | Peptide_P | PFGHLTKLELPTDHH | 74-88 | VP2 | A10 Holland |
| 24 | Peptide_Q | YGKVSNPPRTSFPG | 26-39 | VP3 | Asia 1 |
| 25 | Peptide_R | DVSLAAKHMSNTYLS | 78-92 | VP3 | A10 Holland |
| 26 | Peptide_S | SIINNYYMQQYQNSMD | 20-35 | VP4 | A10 Holland |
| 27 | Peptide_T | YQNSMDTQLGDN | 30-41 | VP4 | Asia 1 |
| 28 | Peptide_U | PFFFSDVRSNFSKLV | 1-15 | 2B | TAW/2/99 |
| 29 | Peptide_V | FFRSTPEDLERAEK | 140-153 | 2B | TAW/2/99 |
| 30 | Peptide_W | LKARDINDIFAILKN | 1-15 | 2C | TAW/2/99 |
| 31 | Peptide_X | SEEKFVTMTDLVPG | 36-50 | 2C | TAW/2/99 |
| 32 | Peptide_Y | VTMTDLVPGILEKQR | 41-55 | 2C | TAW/2/99 |
| 33 | Peptide_Z | YFLIEKGQHEAAIEF | 11-25 | 3A | O1 Kaufbeuren |

TABLE 1-continued

Peptide Sequences From different FMDV Strains

| SEQ ID NO. | Dataset | Sequence | Amino acid residue | Protein region | FMDV strain |
|---|---|---|---|---|---|
| 34 | Peptide_A1 | AAIEFFEGMVHDSIK | 21-35 | 3A | O1 Campos |
| 35 | Peptide_B1 | ERTLPGQKACDDVN | 126-139 | 3A | O1 Kaufbeuren |
| 36 | Peptide_C1 | GPYAGPLETQKPLK | 1-14 | 3B | O1 Kaufbeuren |
| 37 | Peptide_D1 | PLERQKPLKVRAKL | 6-19 | 3B | O1 Kaufbeuren |
| 38 | Peptide_E1 | GPYAGPMERQKPLK | 24-37 | 3B | O1 Kaufbeuren |
| 39 | Peptide_F1 | PMERQKPLKVKAKA | 29-42 | 3B | O1 Kaufbeuren |
| 40 | Peptide_G1 | QKPLKVKAKAPVVK | 33-46 | 3B | O1 Kaufbeuren |
| 41 | Peptide_H1 | PVKKPVALKVKAKN | 52-65 | 3B | O1 Kaufbeuren |
| 42 | Peptide_I1 | NADVGRLIFSGEALT | 121-135 | 3C | O1 Kaufbeuren |
| 43 | Peptide_J1 | AVLAKDGADTFIVGT | 166-180 | 3C | O1 Kaufbeuren |
| 44 | Peptide_K1 | MRKTKLAPTVAIIGVF | 16-30 | 3D | C-S8 |
| 45 | Peptide_L1 | VLDEVIFSKHKGDTK | 51-65 | 3D | C-S8 |
| 46 | Peptide_M1 | TANAPLSIYEAIKGVDGLDAMEPDT | 91-115 | 3D | C-S8 |
| 47 | Peptide_N1 | VDVLPVEHILYTRMMIGRFC | 181-200 | 3D | C-S8 |
| 48 | Peptide_O1 | SATSIINTILNNIYV | 301-315 | 3D | C-S8 |
| 49 | Peptide_P1 | VELDTYTMISYGDDI | 326-340 | 3D | C-S8 |
| 50 | Peptide_Q1 | VVASDYDLDFEALKPHFKSL | 341-360 | 3D | C-S8 |
| 51 | Peptide_R1 | YDLDFEALKPHFKSL | 346-360 | 3D | C-S8 |
| 52 | Peptide_S1 | EALKPHFKSLGQTYT | 351-365 | 3D | C-S8 |
| 53 | Peptide_T1 | HFKSLGQTYTPADKS | 356-370 | 3D | C-S8 |
| 54 | Peptide_U1 | TDVTFLKRHFHMDYGTGFYK | 381-400 | 3D | C-S8 |
| 55 | Peptide_V1 | KTLEAILSFARRGTI | 406-420 | 3D | C-S8 |

TABLE 2

Sequences of Polynucleotide and Carrier Systems

| SEQ ID NO. | Polynucleotide or Protein | Sequence |
|---|---|---|
| 56 | BLS-I $_{(DNA)}$ (Polynucleotide encoding BLS-I) | atgcattacagcagaaatgctgtgcccaacgcgagaggtgacctccaggtgttggctca aaaggtggcaggtagccttaagacatcctttaaaatcgcattcattcaggcccgctggca cgccgacatcgttgacgaagcgcgcaaaagctttgtcgccgaactggccgcaaagac gggtggcagcgtcgaggtagagatattcgacgtgccgggtgcatatgaaattcccctc acgccaagacattggccagaaccgggcgctatgcagccatcgtcggtgcggccttcgt gatcgacggcggcatctatcgtcatgatttcgtggcgacggccgttatcaacggcatgat gcaggtgcagcttgaaacggaagtgccggtgctgagcgtcgtgctgacgccgcaccat ttccatgaaagcaaggagcatcacgacttcttccatgctcatttcaaggtgaagggcgtg gaagcggcccatgccgccttgcagatcgtgagcgagcgcagccgcatcgcgcttgtc |
| 57 | BLS-I (BLS protein fused to SEQ ID NO. 9) | MHYSRNAVPNARGDLQVLAQKVAGSLKTSFKIAFIQAR WHADIVDEARKSFVAELAAKTGGSVEVEIFDVPGAYEI PLHAKTLARTGRYAAIVGAAFVIDGGIYRHDFVATAVI NGMMQVQLETEVPVLSVVLTPHHFHESKEHHDFFHAH FKVKGVEAAHAALQIVSERSRIALV |

TABLE 2-continued

Sequences of Polynucleotide and Carrier Systems

| SEQ ID NO. | Polynucleotide or Protein | Sequence |
|---|---|---|
| 58 | BLS-D (BLS protein fused to SEQ ID NO. 4) | MHETQIQRRQHTDVSFIMDRFVGSLKTSFKIAFIQARWH ADIVDEARKSFVAELAAKTGGSVEVEIFDVPGAYEIPLH AKTLARTGRYAAIVGAAFVIDGGIYRIIDFVATAVTNGM MQVQLETEVPVLSVVLTPHHFHESKEHHDFFHAHFKVK GVEAAHAALQIVSERSRIALV |
| 59 | BLS-A1 (BLS protein fused to SEQ ID NO. 34) | MHAAIEFFEGMVHDSIKGSLKTSFKIAFIQARWHADIVD EARKSFVAELAAKTGGSVEVEIFDVPGAYEIPLHAKTLA RTGRYAAIVGAAFVIDGGIYRHDFVATAVINGMMQVQ LETEVPVLSVVLTPHHFHESKEHHDFFHAHFKVKGVEA AHAALQIVSERSRIALV |
| 60 | BLS-I_A2001 (BLS protein fused to SEQ ID NO. 10) | MHYTVSGLSRRGDLGSLAARVAKGSLKTSFKIAFIQAR WHADIVDEARKSFVAELAAKTGGSVEVEIFDVPGAYEI PLHAKTLARTGRYAAIVGAAFVIDGGIYRHDFVATAVI NGMMQVQLETEVPVLSVVLTPHHFHESKEHHDFFHAH FKVKGVEAAHAALQIVSERSRIALV |

In one embodiment, the universal vaccine can be performed without the polynucleotide sequences.

In one embodiment, the process of the present invention was developed according to GMP standards, in order to ensure the quality and purity of the vaccines. In many cases, compliance with GMP standards is a necessary condition to export the products from the processes.

In one embodiment, the present invention is suitable to qualify as an emergency vaccine under OIE protocol in order to be used against outbreaks for emerging FMDV strains. This qualification is achieved because this vaccine provides animals with sufficient and adequate protection against FMDV infection after a single administration.

In one embodiment, the present invention is suitable to generate antigen banks that could be used in case of emergency in order to formulate a FMDV universal vaccine.

In another embodiment, the vaccine formulations can be administered in multiple doses.

In one embodiment, the present invention provides a vaccine formulation capable of inducing cross-protection against different serotypes and/or strains of Foot and Mouth Disease Virus (FMDV), comprising whole inactivated FMDV with at least one of the following components: a) polynucleotides encoding FMDV peptides, polypeptides or proteins in different types of plasmids; b) synthetic FMDV peptides or polypeptides; c) recombinant FMDV peptides, polypeptides or proteins; d) FMD Virus-Like-Particles: e) virus-like-particles derived from other viruses displaying recombinant FMDV peptides, polypeptides or proteins; f) peptides, polypeptides or proteins used as a carrier or as molecular adjuvant fused to peptides, polypeptides and/or proteins derived from FMDV; g) adjuvants, emulsifiers, molecular adjuvants and carrier systems.

In one embodiment, the above vaccine formulation is capable of inducing protective immunity against all strains of a given serotype of FMDV. In another embodiment, the vaccine formulation is capable of inducing protective immunity against all strains of at one or more of the following serotypes: O. A, C. Asia 1. SAT-1, SAT-2, and SAT-3. In another embodiment, the vaccine formulation is capable of inducing protective immunity against all strains of all serotypes of FMDV.

In one embodiment, the vaccine formulation comprises one or more polynucleotides that encode the entire or partial or variant of FMDV proteins, such as capsid protein genes VP1, VP2, VP3 and VP4; non-structural protein genes 2A, 2B, 2C, 2D, 3A, 3B, 3C and 3D: or any polynucleotide sequences that encode one of the peptides of SEQ ID NO. 1-55 (Table 1) or its variants. In another embodiment, the vaccine formulation comprises polynucleotides that encode peptide(s) homologous to the peptides of Table 1. In yet another embodiment, the vaccine formulation comprises polynucleotides that encode peptide(s) that are functional analogues to the peptides of Table 1.

In one embodiment, the vaccine formulation comprises FMDV peptides, polypeptides or proteins comprising the entire or partial or variant sequences of one or more FMDV proteins such as: capsid proteins VP1, VP2, VP3 and VP4; non-structural proteins 2A, 2B, 2C, 2D, 3A, 3B, 3C and 3D; or peptides of SEQ ID NO. 1-55. In another embodiment, the polypeptides or proteins comprise any amino acid sequences that are homologous or functional analogues to the peptides of Table 1. In yet another embodiment, the FMDV polypeptides are native, synthetic or recombinant peptides and polypeptides derived entirely, partially or mutated from the hypervariable region of the GH loop of the VP1 (135-160) region of FMDV capsid protein and that contain the RGD motif (sequence of 3 amino acids: Arg-Gly-Asp). In one embodiment, the FMDV polypeptides are linear peptides. In another embodiment, the FMDV polypeptides are dendrimeric peptides with different configurations, including but not limited to, random hyperbranched, dendrigraft, dendrons, dendrimers. In one embodiment, the dendrimeric peptides are constructed by fusing FMDV immunogenic peptides only.

In one embodiment, the inactivated FMDV used in the vaccine formulation can originate from any serotype or strain of FMDV. In another embodiment, the vaccine formulation comprises one or more inactivated FMDV originated from different serotypes and/or strains of FMDV.

In one embodiment, the vaccine formulation containing FMD virus-like-particles comprises native or mutated form of one or more of VP0, VP1 and VP3 proteins. In one embodiment, the mutated form of VP0, VP1 or VP3 has the ability to form a whole empty capsid.

In one embodiment, the vaccine formulation containing virus-like-particles derived from other viruses are fused to entire or partial or variant amino acid sequences of one or more FMDV proteins such as: capsid proteins VP1, VP2, VP3 and VP4; non-structural proteins 2A, 2B, 2C. 2D, 3A, 3B, 3C and 3D: or peptides of SEQ ID NO. 1-55; or peptides that are homologous or functional analogues to the peptides of Table 1.

In one embodiment, the vaccine formulation comprises peptides, polypeptides and proteins, used as carriers and/or molecular adjuvants, that are fused to entire or partial or variant amino acid sequences of one or more FMDV peptides, polypeptides and proteins, such as capsid proteins VP1, VP2, VP3 and VP4; non-structural proteins 2A, 2B, 2C, 2D, 3A. 3B, 3C and 3D; peptides of SEQ ID NO. 1-55, or any peptides that are homologous or functional analogues to the peptides of Table 1. In one embodiment, the FMDV polypeptides are native, synthetic or recombinant peptides and polypeptides derived entirely, partially or mutated from the hypervariable region of the GH loop of the VP1 (135-160) region of FMDV capsid protein as described above.

In one embodiment, the protein, polypeptide and peptide carriers can be fused to the target sequences with any linker.

In one embodiment, the proteins used as carriers and/or molecular adjuvants are derived from the native amino acid sequence of Brucella lumazine synthase (BLS) protein or its mutated variants. In one embodiment, the BLS protein is fused to FMDV peptides, polypeptides and proteins by any peptide or polypeptide linker. In one embodiment, the BLS protein used as carrier and/or molecular adjuvants is fused to one or more FMDV peptides, polypeptides or proteins derived entirely, partially or mutated from the capsid proteins (VP1, VP2, VP3 and VP4) or non-structural proteins (2A, 2B, 2C, 2D, 3A, 3B, 3C and 3D). In some embodiments, the BLS proteins used as carriers and/or molecular adjuvants are fused to peptides with FMDV epitopes as shown in Table 1 (SEQ ID NO. 1-55) or their variants, or any peptides that are homologous or functional analogues to the peptides of Table 1. In another embodiment, the FMDV polypeptides are native, synthetic or recombinant peptides and polypeptides derived entirely, partially or mutated from the hypervariable region of the GH loop of the VP1 (135-160) region of FMDV capsid protein as described herein. In another embodiment, the BLS proteins are fused to peptides, polypeptides and proteins with any peptide or polypeptide linker. In one embodiment, the BLS proteins are fused to one or more FMDV peptides, polypeptides and proteins from the same FMDV strain or serotype. In another embodiment, the BLS proteins are fused to one or more FMDV peptides, polypeptides and proteins from different FMDV strains and/or serotypes. In another embodiment, the BLS or their variants are not fused to any FMDV peptides, polypeptides and proteins. In another embodiment, variants of BLS are BLS proteins with point mutations that improve degree of stability.

In one embodiment, the adjuvants and emulsifiers can be aluminium salts, aluminium hydroxide gel, saponine or derivatives, like QS21, lymph cytokines, CpG, poly I:C, toll-like receptors agonists, immune stimulating complexes (ISCOMs), liposomes, incomplete Freund's adjuvant, liposyn, tyrosine stearate, squalene, L121, Emulsigen, monophosphoryl lipid A (MPL), Montanide ISA adjuvants (ISA 15 VG, ISA 25 VG, ISA 28 VG, ISA 35 VG, ISA 201 VG, ISA 206 VG. ISA 207 VG, ISA 50 V2, ISA 50 V4, ISA 61 VG, ISA 70, ISA 71 VG, ISA 71 R VG, ISA 720, ISA 760. ISA 761 VG, ISA 763 A VG, ISA 775, ISA 780), Montanide IMS adjuvants (IMS 251 C, IMS 1312 VG, IMS 1313 VG N, IMS 2215, IMS 3012), Montanide GEL 01, Montanide GEL 02, light mineral oils, metabolisable oils, polysorbate 20, polysorbate 40, polysorbate 60, polysorbate 65, polysorbate 80, polysorbate 85, polysorbate 120, sorbitan monostearate, sorbitan tristearate, sorbitan monolaurate, sorbitan monooleate, sorbitan trioleate, sorbitan monopalmitate and other efficacious adjuvants and emulsifiers.

In one embodiment, the vaccine formulation is an emulsion, such as water-in-oil emulsion (W/O) or an oil-in-water (O/W) emulsion or a water-in-oil-in water emulsion (W/O/W) or an oil-in-water-in oil (O/W/O) emulsion. In another embodiment, the vaccine formulation comprises a mix of an emulsion and one or more additional adjuvants.

In one embodiment, the carrier systems can be liposomes, microspheres, nanoparticles, dendrimers, micellar systems or immune stimulating complexes (ISCOMs).

The present invention also provides a method of vaccinating a host susceptible to FMDV infection, comprising administrating to the host the vaccine formulation described above to induce an immune response. In one embodiment, the components of the vaccine formulations described in the present invention are administered separately to the host. In another embodiment, the components of the vaccine formulations are administrated at the same time, but in different locations of the host body. In another embodiment, the components of the vaccine formulations are administrated at different time points in different locations of the host body. In one embodiment, the host is a cattle, sheep, goats or swine.

In one embodiment, the host has not been infected with FMDV and the induced immune response is a protective immune response. In another embodiment, the host has been infected with FMDV and the induced immune response is a therapeutic immune response. In one embodiment, the induced immune response is humoral immune response. In another embodiment, the immune response is cellular immune response. In another embodiment, the induced immune response comprises cross-protective neutralizing antibodies against various serotypes and/or strains of FMDV. In yet another embodiment, the induced immune response cross-reacts against various serotypes and/or strains of FMDV.

In one embodiment, the present invention discloses a vaccine formulation capable of inducing cross-protection against different serotypes or strains of a virus, comprising whole inactivated virus and at least one of the following components: (a) polynucleotides encoding peptides, polypeptides or proteins of the virus; (b) synthetic peptides or polypeptides of the virus; (c) recombinant peptides, polypeptides or proteins of the virus; (d) virus-like-particles of the virus; (e) virus-like-particles derived from other viruses displaying recombinant peptides, polypeptides or proteins of the virus; and (f) peptides, polypeptides or proteins as carriers or molecular adjuvants that are or are not fused to above peptides, polypeptides or proteins of the virus. The virus includes but not limited to FMDV, Bovine Rotavirus, BoHV-1 and BoHV-5, BPIV-3, BRSV, BVDV and Rabies Virus.

In one embodiment, the vaccine formulation is capable of inducing protective immunity against all strains of a given serotype of said virus, or against all strains of all serotypes of said virus.

In one embodiment, the vaccine formulation is against FMDV and the polynucleotides in the formulation are derived from the entire, partial or variant sequences of: (a) polynucleotide sequences encoding one or more of FMDV capsid protein genes VP1, VP2, VP3 and VP4; (b) polynucleotide sequences encoding one or more of FMDV non-structural protein genes 2A. 2B, 2C, 2D, 3A, 3B, 3C and 3D: (c) polynucleotide sequences encoding one or more of peptides of SEQ ID NO. 1-55: or (d) polynucleotide sequences encoding peptides that are homologous to the peptides of Table 1. In one embodiment, homologous peptides may have 55, 60, 65, 70, 75, 80, 85, 90 or 95% homology to SEQ ID NO.1-55. In one embodiment, the polynucleotide sequences encode peptides that are functional analogues to the peptides of Table 1. In one embodiment, functional analogues peptides may only have as low as 10% amino acid sequence homology to any one of SEQ ID NO.1-55.

In another embodiment, the vaccine formulation is against FMDV and the recombinant or synthetic viral peptides, polypeptides or proteins are encoded by the entire, partial or variant sequences of: (a) amino acid sequences of FMDV capsid proteins VP1, VP2, VP3 and VP4; (b) amino acid sequences of FMDV non-structural proteins 2A, 2B, 2C, 2D, 3A, 3B, 3C and 3D: (c) amino acid sequences of one or more of SEQ ID NO. 1-55; or (d) amino acid sequences that encode peptides which are homologous or functional analogues to the peptides of Table 1. In one embodiment, homologous peptides may have 55, 60, 65, 70, 75, 80, 85, 90 or 95% homology to SEQ ID NO.1-55. In another embodiment, functional analogues peptides may only have as low as 10% amino acid sequence homology to any one of SEQ ID NO.1-55. In one embodiment, the recombinant or synthetic viral peptides or polypeptides are linear or dendrimeric peptides. In another embodiment, the vaccine formulation comprises inactivated FMDV derived from any serotype or strain of FMDV. In one embodiment, the inactivated FMDV comprises one or more serotypes or strains of FMDV. In another embodiment, the vaccine formulation comprises virus-like-particles of FMDV comprising native or mutated form of one or more of FMDV VP0, VP1 and VP3 proteins, or mutated form of VP0, VP1 or VP3 that has the ability to form a whole empty capsid.

In one embodiment, the vaccine formulation is against FMDV and the virus-like-particles in the formulation are derived from other viruses, wherein the virus-like-particles are fused to entire, partial or variant sequences of: (a) amino acid sequences of FMDV capsid proteins VP1, VP2, VP3 and VP4; (b) amino acid sequences of FMDV non-structural proteins 2A, 2B, 2C, 2D, 3A, 3B, 3C and 3D: (c) amino acid sequences that are homologous or functional analogues to the peptides of Table 1. In one embodiment, homologous peptides may have 55, 60, 65, 70, 75, 80, 85, 90 or 95% homology to SEQ ID NO.1-55. In another embodiment, functional analogues peptides may only have as low as 10% amino acid sequence homology to any one of SEQ ID NO. 1-55.

In another embodiment, the vaccine formulation is against FMDV and the carriers or molecular adjuvants are fused to entire, partial or variant of: (a) amino acid sequences of FMDV capsid proteins VP1, VP2, VP3 and VP4; (b) amino acid sequences of FMDV non-structural proteins 2A. 2B, 2C, 2D. 3A, 3B, 3C and 3D; (c) amino acid sequences of one or more of SEQ ID NO. 1-55; or (d) amino acid sequences that are homologous or functional analogues to the peptides of Table 1. In one embodiment, homologous peptides may have 55, 60, 65, 70, 75, 80, 85, 90 or 95% homology to SEQ ID NO.1-55. In another embodiment, functional analogous peptides may only have as low as 10% amino acid sequence homology to any one of SEQ ID NO.1-55. In one embodiment, the carriers or molecular adjuvants are linear or dendrimeric.

In another embodiment, the carriers or molecular adjuvants are derived from native amino acid sequence of *Brucella* lumazine synthase (BLS) protein or its mutated variants. In one embodiment, the BLS protein is fused to one or more FMDV peptides, polypeptides or proteins derived from a same FMDV strain or serotype. In another embodiment, the BLS protein is fused to one or more FMDV peptides, polypeptides or proteins derived from different FMDV strains or serotypes. In one embodiment, the BLS protein or its variants are not fused to any FMDV peptides, polypeptides and proteins. In another embodiment, the variants of BLS are BLS proteins with point mutations to improve its degree of stability.

The present invention also provides a method of vaccinating a host susceptible to FMDV infection, comprising administrating to the host the vaccine formulation described above to induce an immune response. In some embodiments, the components of the vaccine formulation are administrated at the same time, but in different locations of the host. In certain embodiments, the components of the vaccine formulation are administrated at different times points in the same location of the host. In one embodiment, the components of the vaccine formulation are administrated at different time points in different locations of the host. The host is a cattle, sheep, goats or swine.

In one embodiment, the host has not been infected with FMDV and the induced immune response is a protective immune response. In another embodiment, the induced immune response is humoral immune response or cellular immune response.

In one embodiment, the induced immune response comprises cross-protective neutralizing antibodies against various serotypes or strains of FMDV. In another embodiment, the induced immune response cross-reacts against various serotypes or strains of FMDV.

The present invention further provides a pharmaceutical combination for inducing one or more immune responses towards one or more viral diseases in a host and/or for enhancing effectiveness of vaccination in the host, comprising: a) one or more vaccine formulations as described above capable of eliciting the immune responses in the host; and b) one or more molecular adjuvants which enhances the immune responses in the host, wherein the vaccine formulations and the molecular adjuvants can be administered separately or together. Examples of viral diseases include, but are not limited to, diseases caused by viruses such as FMDV, Bovine Rotavirus, BoHV-1 and BoHV-5, BPIV-3, BRSV, BVDV and Rabies Virus. In one embodiment, the pharmaceutical combination is a vaccine formulation comprising one or more polynucleotides, peptides, polypeptides, proteins, virus-like-particles, inactivated virus, adjuvants, emulsifiers, molecular adjuvants and carrier systems described in the present invention. In another embodiment, the pharmaceutical combination comprises one or more vaccine formulations comprising one or more polynucleotides, peptides, polypeptides, proteins, virus-like-particles, inactivated virus, adjuvants, emulsifiers, molecular adjuvants and carrier systems described in the present invention.

In some embodiments, the vaccine formulation used in the pharmaceutical combination of the present invention can induces cross-protection against different serotypes and/or strains of a target virus such as FMDV, Bovine Rotavirus, BoHV-1 and BoHV-5, BPIV-3. BRSV, BVDV and Rabies Virus. In some embodiments, the vaccine formulation of the present invention comprises one or more components in an effective amount to trigger the immune responses, e.g. adjuvants, emulsifiers, molecular adjuvants and carriers. The components used in the vaccine formulation to trigger the immune responses include but not limited to: whole inactivated virus: virus-like-particles; virus-like-particles derived from other viruses displaying recombinant viral peptides, polypeptides or proteins; polynucleotides encoding viral peptides, polypeptides or protein; synthetic peptides or polypeptides of the target virus; recombinant peptides, polypeptides or proteins of the target virus; virus-like-particles of the target virus; virus-like-particles derived from other viruses.

In one embodiment, the molecular adjuvant of the pharmaceutical combination is selected from the group consisting of aluminium salts, aluminium hydroxide gel, saponine or derivatives, like QS21, lymph cytokines, CpG, poly I:C, toll-like receptors agonists, immune stimulating complexes (ISCOMs), liposomes, incomplete Freund's adjuvant, liposyn, tyrosine stearate, squalene, L121. Emulsigen, monophosphoryl lipid A (MPL), Montanide ISA adjuvants (ISA 15 VG, ISA 25 VG, ISA 28 VG, ISA 35 VG, ISA 201 VG, ISA 206 VG, ISA 207 VG, ISA 50 V2, ISA 50 V4, ISA 61 VG, ISA 70, ISA 71 VG, ISA 71 R VG, ISA 720, ISA 760, ISA 761 VG, ISA 763 A VG, ISA 775, ISA 780), Montanide IMS adjuvants (IMS 251 C, IMS 1312 VG, IMS 1313 VG N, IMS 2215, IMS 3012), Montanide GEL 01, Montanide GEL 02, light mineral oils, metabolisable oils, polysorbate 20, polysorbate 40, polysorbate 60, polysorbate 65, polysorbate 80, polysorbate 85, polysorbate 120, sorbitan monostearate, sorbitan tristearate, sorbitan monolaurate, sorbitan monooleate, sorbitan trioleate, sorbitan monopalmitate, a water-in-oil emulsion (W/O), an oil-in-water (O/W) emulsion, a water-in-oil-in-water emulsion (W/O/W), an oil-in-water-in-oil (O/W/O) emulsion, poly(lactic-co-glycolic) acid, polysaccharides, dendrimers, gold nanoparticles, antigenic epitopes derived from capsid protein of the viruses, Brucella Lumazine Synthase (BLS) protein, BLS protein fused to the components which can trigger immune responses or mutated variants of BLS protein fused to the components which can trigger the immune responses.

In one embodiment, the BLS protein is fused to the components which can trigger immune responses by peptide or polypeptide linker.

The present invention further provides a method of vaccinating a host susceptible to virus infection, comprising administrating to the host the pharmaceutical combination of the present invention to induce an immune response, wherein the vaccine and the molecular adjuvant are administered to the host separately or together.

In one embodiment, the pharmaceutical combination can be administered by syringe injection, needle free injection, microneedle patch and delivery.

In one embodiment, the pharmaceutical combination can be administered at the same time and same body location of the host. In another embodiment, the pharmaceutical combination can be administered at different time and at the same body location of the host. In another embodiment, the pharmaceutical combination can be administered at the same time and at different body location of the host. In another embodiment, the pharmaceutical combination can be administered at different time and at different body location of the host.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including". "containing" or "characterized by", is inclusive or open-ended and does not exclude additional, un-recited elements or method steps.

Example 1

Preparation of Vaccine Formulations

This example illustrates the formulation and the procedures for obtaining different types of vaccine against FMDV.

In one embodiment, the vaccine formulations featuring recombinant proteins or inactivated whole FMDV viral antigens comprise the following chemical substances and solutions:

Aqueous phase (antigenic phase) solution: Tris(hydroxymethyl)aminomethane (Tris) 0.02 M, NaCl 0.3 M. pH=8.
Oil phase solution: Montanide ISA 50 V2.

In another embodiment, the vaccine formulation featuring plasmid DNA comprises the following chemical substances and solutions:

Phosphate Buffer Saline 10×(PBS): 80 g/L NaCl, 2 g/L KCl, 11.5 g/L $Na_2HPO_4$. 2 g/L $KH_2PO_4$. pH=7.2.

Table 3 shows the four different vaccine formulations to be tested (D, E. F and G).

TABLE 3

Formulations of three BLS based FMDV recombinant vaccines and one inactivated viral antigens vaccine

| Vaccine formulations | D | E | F | G |
|---|---|---|---|---|
| Type of vaccine | Plasmid DNA | Recombinant protein | Recombinant proteins | Inactivated whole viral antigens - 4 strains |
| Antigenic Components | BLS-I$_{(DNA)}$ 1 mg/dose (in PBS buffer) | BLS-I 845 ug/dose | BLS-I 415 ug/dose, BLS-D 400 ug/dose, BLS-A1 560 ug/ds | O1 Campos 14.8 ug/dose, A 24 Cruzeiro 4.2 ug/dose, C3 Indaial 7.1 ug/dose, A2001 8.9 ug/dose |
| Homogenizer | — | Ultraturrax | Ultraturrax | Silverson |
| Type of emulsion | — | Single oil | Single oil | Single oil |
| Saponine | — | — | — | 1 mg/ds |
| Oil phase/Aqueous phase relation | — | 60:40 | 60:40 | 60:40 |
| Aqueous phase volume (mL) | — | 31.3 | 31.3 | 2000 |

TABLE 3-continued

Formulations of three BLS based FMDV recombinant vaccines and one inactivated viral antigens vaccine

| Vaccine formulations | D | E | F | G |
|---|---|---|---|---|
| Oil phase volume (mL) | — | 47.0 | 47.0 | 3000 |
| Total Antigenic Mass (ug/dose) | 1000 | 845 | 1375 | 35 |
| Total vaccine volume (mL) | 100 | 78.3 | 78.3 | 5000 |

In one embodiment, the BLS based recombinant proteins FMD vaccines were formulated according to the following procedure:
1) The aqueous phase was prepared in a conical tube of 50 mL with the volumes indicated in Table 3.
2) The volume of the oil phase was added in a 100 mL beaker.
3) The small stem (S10N-10G, S10N-10G-ST, S18N-10G, S18N-19G, S25N-10G, S25N-10G-ST, S25N-18G. S25N-18G-ST, S25N-25G, S25N-25G-ST and other similar) of the Ultra-Turrax (T10, T18, T25 or T50) was placed inside the tube with the oil phase. While this phase was stirred at 6500 rpm, the appropriate volume of aqueous phase was added at a flow rate of 5 mL/min.
4) Once all the aqueous phase was added, the mixture was emulsified for 30 seconds at 21500 rpm.
5) 500 ul of each formulation was aliquoted in an Eppendorf tube in order to measure the distribution of particles sizes. If the value of d(0.9) (the $90^{th}$ percentile, which indicates that 90% of the volume of the aqueous phase has formed particles featuring a diameter smaller than the indicated size (μm)) was less than 3 microns, the experiments proceeded to fill and finish. Otherwise, it was homogenized for an additional 30 seconds and the d(0.9) re-measured to obtain the specified value.
6) The formulations were aseptically fractioned in 25 mL vials which were subsequently closed and capped with rubber stopper and flip off using sterile tweezers.
7) The different formulations were stored at 4° C.

In another embodiment, the BLS based plasmid DNA FMD vaccine was formulated according to the following procedure:
1) The plasmid pVAX1 with the BLS-I$_{(DNA)}$ was purified by QIAGEN's EndoFree Plasmid Giga Kit from a culture of *E. coli* DH5α in LB animal-free/kanamicine 50 μg/mL at 37° C.
2) The presence of the plasmid pVAX1-BLS-I$_{(DNA)}$ was confirmed by agarose gel electrophoresis.
3) The purified plasmid pVAX1-BLS-I$_{(DNA)}$ was diluted to a final concentration of 1 mg/mL using 10×PBS buffer.

In another embodiment, the inactivated whole viral antigens FMD vaccine was formulated according to the following procedure:
1) The oily phase was mixed energetically using a magnetic stirrer in a sterile 5-liters glass bottle.
2) The aqueous phase, prepared in a second 5-liters sterile glass bottle and with the inactivated whole viral FMD antigens obtained from the production process was transferred gradually to the first 5-liters bottle containing the oily phase with constant mixing of the two phases at 13.5-15° C., using a peristaltic pump and sterile silicone tubings.
3) The temperature was decreased to 2-8° C. and an energetic agitation using magnetic stirrer was maintained for 15-16 hours approximately.
4) The blend was then transferred from the first 5-liters bottle to a third new and sterile 5-liters glass bottle passing through the pilot-scale high-shear Silverson emulsifier L4RT to produce the final emulsion. The rotation speed of the high-shear Silverson emulsifier L4RT used was 4000 rpm.
5) The emulsion was stirred for additional 30-35 minutes after the completion of the emulsion process.
6) Stirring was stopped and the emulsion was kept at rest at 2-8° C. until the time of fill and finish.

Example 2

Vaccination with BLS Based FMDV Recombinants Peptides (O1 Campos) Vaccines

This example illustrates the procedure to vaccinate animals with different vaccine formulations, including BLS based FMDV Recombinants Vaccines.
(a) Animal Model:
The study was performed with 22 Hereford calves between 18 and 24 months old, which had not been previously immunized with FMD vaccine. All animals were tested for serology against FMDV whereby the absence of colostral antibody and/or vaccine related antibodies was confirmed. The animals remained in the field throughout the entire clinical trial.
(b) Experimental Groups:
The animals were randomly divided into six experimental groups: Group 1 (n=4) was immunized with 1 mL of vaccine formulation D (Table 3, SEQ ID NO. 56: BLS-I$_{(DNA)}$ plasmid DNA (pVAX1) encoding fusion protein BLS-I) and 5 ml of formulation E (Table 3, SEQ ID NO. 57: BLS-I) at different times; Group 2 (n=4) was immunized with 1 mL of vaccine formulation D (Table 3, SEQ ID NO. 56: BLS-I$_{(DNA)}$ plasmid DNA (pVAX1) encoding fusion protein BLS-I) and 5 ml of formulation F (combination of fusion proteins SEQ ID NO. 57 (BLS-I), SEQ ID NO. 58 (BLS-D), and SEQ ID NO. 59 (BLS-A1) as described in Table 3) at different times; Group 3 (n=4) was immunized twice with 5 mL of vaccine formulation E (Table 3, SEQ ID NO. 57: BLS-I) at different times: Group 4 (n=4) was immunized twice with 5 mL of vaccine formulation F (combination of fusion proteins SEQ ID NO. 57 (BLS-I), SEQ ID NO. 58 (BLS-D), and SEQ ID NO. 59 (BLS-A1) as described in Table 3) at different times; Group 5 (n=2) corresponds to the control group whose animals were not vaccinated. Finally, Group 6 (n=4) was immunized with 2 mL of vaccine formulation G (tetravalent vaccine comprising four inactivated FMDV antigens as positive control as described in Table 3).

TABLE 4

Different schemes of vaccination

| Group number | Immunization strategy | Number of animals | 1st dose (Prime) (t = 0 dpv) | 2nd dose (Boost) (t = 30 dpv) |
|---|---|---|---|---|
| Group 1 | DNA/Protein | 4 | Vaccine D ID 1 ml/dose | Vaccine E IM 5 ml/dose |
| Group 2 | DNA/Protein | 4 | Vaccine D ID 1 ml/dose | Vaccine F IM 5 ml/dose |
| Group 3 | Protein/Protein | 4 | Vaccine E IM 5 ml/dose | Vaccine E IM 5 ml/dose |
| Group 4 | Protein/Protein | 4 | Vaccine F IM 5 ml/dose | Vaccine F IM 5 ml/dose |
| Group 5 | Non-vaccinated controls | 2 | — | — |
| Group 6 | Positive control: inactivated viral antigens vaccine | 4 | Vaccine G IM 2 ml/dose | — |

ID: Intradermal injection
IM: Intramuscular injection (c) Vaccination Schemes:
Experimental vaccines were administered on days 0 and 30 of the study using a prime/boost strategy: the first injection at day 0 represents the priming immunization and the second injection at day 30 represents the boosting immunization.

(d) Bleedings:
Bleedings at 30, 60, 90 and 105 days post vaccination (DPV) were performed. Table 4 shows the different schemes of vaccination.

(e) Serology Against FMDV
ELISA assays were performed in order to measure total O1 Campos strain specific antibodies produced when the vaccine formulations comprised of DNA (BLS-I) with BLS-peptide (BLS-D, BLS-I and BLS-A1) (FIGS. 1 and 2, Groups 1 and 2) and mixture of BLS-peptides (different combinations of BLS-D, BLS-I and BLS-A1) (FIGS. 1 and 2, Groups 3 and 4) were applied in bovines (2 or 5 mL dose per formulation). The results showed that both types of vaccines could only induce very low antibodies production, at a notably lower level than the positive control (FIGS. 1 and 2. Group 6).

Example 3

Infectious Challenge

This example illustrates the results of protection obtained when the animals vaccinated as in example 2 are challenged against the FMDV strain O1 Campos.

At 112 days after the first vaccination (DPV), the animals from example 2 were challenged with 10000 lethal dose 50 (LD50) (lethal doses determined in suckling mice) by intra-lingual injection of virulent FMDV O1 Campos strain in a Biosafety level 4 OIE facility (BSL-4 OIE). Results of protection from podal generalization (PPG) were read at 7 days post-infection (dpi). Animals were defined as "protected" when their members, right fore member (RFM), left fore member (LFM), right hind member (RHM) and left hind member (LHM), do not show any symptom. The tongue is not taken into account for analysis because it is the inoculation site.

Results: An infectious challenge was made in order to test whether these vaccines were capable of conferring protective immunity. The results showed that these vaccines were not able to protect the animals against the virus as all of them presented typical FMDV-associated lesions. Only the inactivated whole FMDV vaccine used as positive control was capable of providing total protection (FIG. 3). The results of these experiments demonstrated that these peptides vaccines, used as sole antigen, were not able to provide to the vaccinated animals any protection against an autologous FMDV challenge.

Example 4

Vaccination with BLS-FMDV Recombinants Peptide (O1 Campos) Vaccine in Combination with Whole Inactivated FMDV (A2001) Vaccine This example illustrates the effect achieved in vaccinating animals with BLS-FMDV recombinants vaccines in combination with whole inactivated FMDV.

(a) Preparation of vaccine formulations:
In one embodiment, the vaccine formulations comprise following chemical substances and solutions:
Aqueous phase solution: Tris(hydroxymethyl)aminomethane (Tris) 0.02 M. NaCl 0.3 M. pH=8.
Oil phase solution: Montanide ISA 61 VG
Vaccine A was formulated using the same procedure as the vaccines in the EXAMPLE 1 that have BLS peptides.
Vaccines B and C were formulated using the same procedure as the vaccine in the EXAMPLE 1 that contains whole inactivated viral antigens.
Table 5 shows three different formulations to be tested (A, B and C).

TABLE 5

Formulation of the vaccines

| Vaccines | A | B | C |
|---|---|---|---|
| Components | BLS-I[(1)] | Monovalent A2001[(2)] | Monovalent O1 Campos[(3)] |
| Homogenizer | Ultraturrax | Silverson | Silverson |
| Type of emulsion | Single oil | Single oil | Single oil |
| Saponine | — | 3 mg/dose | 3 mg/dose |
| Oil phase/Aqueous phase relation | 60:40 | 60:40 | 60:40 |
| Quantity of dose (2 ml/dose) | 6 | 2500 | 2500 |
| Aqueous phase volume (mL) | 4.8 | 2000 | 2000 |
| Oil phase volume (mL) | 7.2 | 3000 | 3000 |
| Antigenic Mass (ug/dose) | 1000 | 10 | 15 |
| Total vaccine volume (mL) | 12 | 5000 | 5000 |

[(1)]BLS-I (SEQ ID NO. 57): BLS protein expressing the immunogenic peptides I at the N-amino end; Peptide I (SEQ ID NO. 9): amino acids 136-156 of the VP1 protein of the FMDV strain O1 Campos.
[(2)]Monovalent A2001: Inactivated FMDV serotype type A2001 whole virus
[(3)]Monovalent O1 Campos: Inactivated FMDV serotype type O1 Campos whole virus (b) Animal Model:
25 Black Aberdeen Angus calves (male and female) between 6 and 10 months old, which have not been immunized with FMD vaccine, were recruited. All animals were tested by serology against FMDV whereby it was confirmed the absence of colostral antibody and/or vaccine related antibodies. The animals remained in the field throughout the entire clinical trial.

(c) Experimental Groups:
The animals were randomly divided into four experimental groups: Group 1 (n=6) was immunized with 2 mL of vaccine formulation B (strain A Argentina 2001) on the right side and simultaneously with 2 mL of vaccine formulation A (Table 5, BLS-I) on the left side. Group 2 (n=6) was immunized with 2 mL of vaccine formulation B (Table 5, strain A Argentina 2001): Group 3 (n=9) was immunized with 2 mL of vaccine formulation C (Table 5, strain O1 Campos): Finally, Group 4 (n=2) corresponds to the control group whose animals were not vaccinated.

(d) Vaccination Schemes:

Experimental vaccines were administered only on day zero of the study. Table 6 shows the different schemes of vaccination.

TABLE 6

Scheme of Vaccination

| Group number | Vaccination strategy | Description | Day 0 | Day 29 | Day 58 |
|---|---|---|---|---|---|
| 1 | A + B | BLS-I + Viral A2001 | Vaccination | Bleeding (serum) | Bleeding (serum) |
| 2 | B | Viral A2001 | Vaccination | Bleeding (serum) | Bleeding (serum) |
| 3 | C | Viral O1-Campos | Vaccination | Bleeding (serum) | Bleeding (serum) |
| 4 | Non vaccinated | Non vaccinated | — | Bleeding (serum) | Bleeding (serum) |

(e) Bleedings:

Bleedings at 29 and 58 days post vaccination (DPV) were performed as shown in Table 6.

(f) Serology Against FMDV

These analyses were performed using a Liquid-Phase ELISA assay specific for O1 Campos antibodies. At both time points after vaccination, 29 DPV and 58 DPV, the antibodies titers obtained in the groups immunized with monovalent viral vaccines were within expected values, with maximum values obtained in the case of homologous O1 Campos vaccine while minimum cross-reactive antibodies against O1 Campos were obtained in animals vaccinated with strain A2001. The immunization strategy combining 2 different vaccines, the recombinant BLS-I vaccine on one side+the whole inactivated A2001 antigen on the other side was able to generate a noticeably good level of antibodies against O1 Campos (FIGS. 4 and 5).

The BLS protein was used here as a carrier and a molecular adjuvant in order to redirect the immune response towards a specific strain or serotype. Experimentation utilizing BLS-I (SEQ ID NO. 57), the protein carrier BLS fused to a peptide with FMDV epitope, showed that a strong immune response against the strain O1 Campos was induced when using a vaccination strategy featuring the combination of the two different vaccines, the A2001 whole inactivated virus vaccine and the fusion peptide BLS-I (SEQ ID NO. 57) vaccine, inoculated at the same time but at different site on the animal (FIGS. 4 and 5). On the other hand, the vaccine that comprises A2001 whole inactivated virus alone, without the fusion peptide BLS-I, failed to generates a good level of antibodies O1 Campos. Also, based on the very poor level of O1 Campos specific antibodies obtained by the BLS-I immunogen alone as evidenced in Example 2, the serology results obtained for the combined immunization strategy are surprisingly high.

Example 5

Vaccination with BLS-FMDV Recombinants Peptide (A2001) Vaccine in Combination with Whole Inactivated FMD O1 Campos Virus Vaccine Three vaccine formulations were tested in bovines in order to analyze whether an immunization strategy combining 2 vaccines, one formulated with A2001 peptides fused to the BLS protein and another one containing whole inactivated O1 Campos virus particles, can trigger a proper immunological response against A2001 in those animals. The vaccines formulations and combinations tested were: I (A2001 whole inactivated virus particles as positive control), J (O1 Campos whole inactivated virus particles as negative control) and H+J (combination of two different vaccines, one vaccine featuring BLS-I_A2001 fusion proteins SEQ ID NO. 60 (H) and the whole inactivated O1 Campos virus particles vaccine (J) (Table 7).

(a) Preparation of Vaccine Formulations

In one embodiment, the vaccine formulations comprise following chemical substances and solutions:

Aqueous phase solution: Tris(hydroxymethyl)aminomethane (Tris) 0.02 M, NaCl 0.3 M. pH=8.

Oil phase solution: Montanide ISA 61 VG

Vaccine H was formulated using the same procedure as the vaccines in the EXAMPLE 1 that have BLS peptides.

Vaccines I and J were formulated using the same procedure as the vaccine in the EXAMPLE 1 that contains whole inactivated viral antigens.

(b) Animal Model:

This study was performed with 38 Hereford calves between 18 and 24 months old, which had not been immunized with FMD vaccine. All animals were tested by serology against FMDV whereby it was confirmed the absence of colostral antibody and/or vaccine related antibodies. The animals remained in the field throughout the entire clinical trial. Table 9 shows the scheme of the infectious challenge.

(c) Vaccination Schemes:

Experimental vaccines were administered on day zero or day zero and day 28. Table 8 shows the different schemes of vaccination.

TABLE 7

Vaccine formulations

| Vaccines | H | I | J |
|---|---|---|---|
| Components | BLS-I_A2001[1] | Monovalent A2001[2] | Monovalent O1 Campos[3] |
| Homogenizer | Ultraturrax | Silverson | Silverson |
| Type of emulsion | Single oil | Single oil | Single oil |
| Saponine | — | 3 mg/dose | 3 mg/dose |
| Oil phase/Aqueous phase relation | 60:40 | 60:40 | 60:40 |
| Quantity of dose (2 ml/dose) | 12 | 2500 | 2500 |
| Aqueous phase volume (mL) | 9.6 | 2000 | 2000 |
| Oil phase volume (mL) | 14.4 | 3000 | 3000 |
| Antigenic Mass (ug/dose) | 1000 | 20 | 20 |
| Total vaccine volume (mL) | 24 | 5000 | 5000 |

[1]BLS-I_A2001 (SEQ ID NO. 60): BLS protein expressing the immunogenic peptides I_A2001 at the N-amino end; Peptide I_A2001 (SEQ ID NO. 10): amino acids 136-156 of the VP1 protein of the FMDV strain A2001.
[2]Monovalent A2001: Inactivated FMDV serotype type A2001 whole virus
[3]Monovalent O1 Campos: Inactivated FMDV serotype type O1 Campos whole virus (d) Bleedings:

Bleedings at 28, 63 and 98 days post vaccination (DPV) were performed as shown in Table 8.

TABLE 8

Scheme of Vaccination

| Group number | Vaccination strategy | Description | Day 0 | Day 28 | Day 63 | Day 98 |
|---|---|---|---|---|---|---|
| 1 | H + J/H | BLS-I_A2001 + Viral O1 Campos | Vaccination | Bleeding (serum) + Vaccination | Bleeding (serum) | Bleeding: (serum) |
| 2 | I | Viral A2001 (positive control) | Vaccination | Bleeding (serum) | Bleeding (serum) | Bleeding: (serum) |
| 3 | J | Viral O1 Campos (negative control) | Vaccination | Bleeding (serum) | Bleeding (serum) | Bleeding: (serum) |
| 4 | Non Vaccinated | Non vaccinated | — | Bleeding (serum) | Bleeding (serum) | Bleeding (serum) |

TABLE 9

The animals were randomly divided into four experimental groups

| Group number | Immunization strategy | Number of animals | 1st dose (t = 0 dpv) | 2nd dose (t = 28 dpv) |
|---|---|---|---|---|
| 1 | BLS_I_A2001 + O1 Campos | 12 | Vaccine H IM 2 ml/dose (RS) Vaccine J IM 2 ml/dose (LS) | Vaccine H IM 2 ml/dose |
| 2 | A2001 (positive control) | 12 | Vaccine I IM 2 ml/dose | — |
| 3 | O1 Campos (negative control) | 12 | Vaccine J IM 2 ml/dose | — |
| 4 | Non vaccinated | 2 | — | — |

Figure 7:
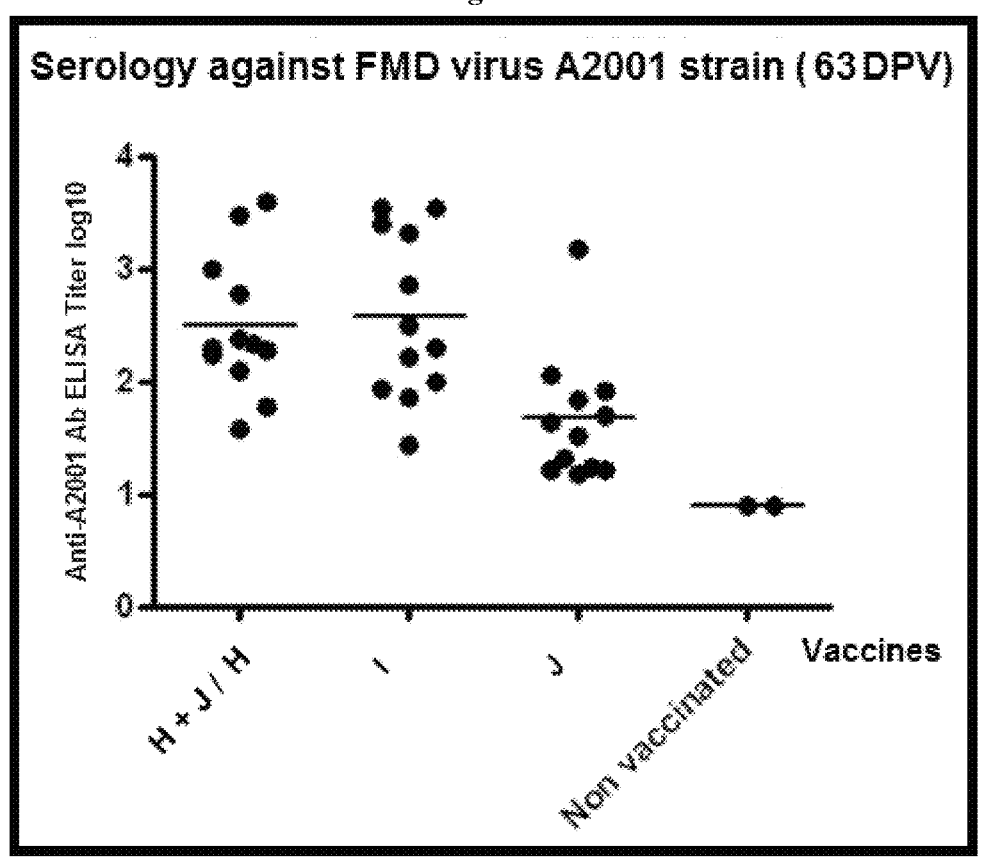

IM: Intramuscular injection;
LS: Left side;
RS: Right side (e) Serology Against FMDV ELISA assays were performed in order to measure total antibodies against A2001 strain produced when these three vaccines were tested. The results showed that the combination of whole inactivated O1 Campos virus particles and BLS-I_A2001 could induce antibodies production at the same level as the positive control (A2001 whole virus vaccine) while the vaccination with the O1 Campos vaccine alone yielded very low anti-A2001 serology results (FIGS. 6 and 7). These results are consistent with those obtained in the example 4 and demonstrate that the surprising synergic effect of this strategy already shown in Example 4 can be used to target any other FMDV strain: success was achieved in the present example just by changing the strain of the whole inactivated virus (O1 Campos) and the fusion peptide (BLS-I_A2001). The results of examples 4 and 5 therefore demonstrate that the strategy and methods described in the present invention effectively enable to obtain a universal FMD vaccine.

Example 6

Infectious Challenge

This example illustrates the results of protection obtained when the animals vaccinated from the example 5 are challenged against the FMDV strain A2001.

At 112 days after the first vaccination (DPV), the animals from example 5 were challenged with 10000 lethal dose 50 (LD50) (lethal doses determined in suckling mice) by intra-lingual injection of virulent FMDV A2001 strain in a Biosafety level 4 OIE facility (BSL-4 OIE). Results of protection from podal generalization (PPG) were read at 7 days post-infection (dpi). Animals were defined as "protected" when their members, right fore member (RFM), left fore member (LFM), right hind member (RHM) and left hind member (LHM), do not show any symptom. The tongue is not taken into account for analysis because it is the inoculation site.

Results: An infectious challenge was made in order to test whether these vaccines were capable of conferring protective immunity. The results showed that the combination between O1 Campos whole inactivated virus particles vaccine (Vaccine J) and the BLS protein fused to A2001 peptides (Vaccine H) was able to protect 7 of 12 animals in Group 1 of Example 6, providing total protection for those animals. Thus, comparing these results with those obtained with O1 Campos whole inactivated virus particles vaccine alone (Example 5, Group 3, Vaccine J, negative control, 0/6 protected) it is clear that the BLS-1_A2001 peptide is capable to redirect the immunological response against the A2001 strain and work synergistically with the whole virus based vaccine of O1 Campos strain in order to protect against the virus A2001 challenge. Therefore, the results of these experiments demonstrate that these peptides vaccines combined with an inactivated whole FMDV vaccine have shown a very surprising and unforeseen effect of stimulation of the immune system and are able to generate a proper cross-protection in the vaccinated animals against heterologous strains.

Example 7

Vaccination with BLS-FMDV Recombinant Peptide (A2001) Antigens in Combination with Whole Inactivated FMD O1 Cameos Virus Formulated in the Same Vaccine This example illustrates that the effect achieved by vaccinating animals with BLS-FMDV recombinants antigens formulated with whole inactivated FMDV in the same vaccine is similar to the effect achieved in Example 5 when the BLS-FMDV antigen and the whole inactivated FMDV are applied separately.

(a) Preparation of Vaccine Formulations

In one embodiment, the vaccine formulations comprise following chemical substances and solutions:

Aqueous phase solution: Tris(hydroxymethyl)aminomethane (Tris) 0.02 M, NaCl 0.3 M. pH=8.

Oil phase solution: Montanide ISA 61 VG

Three different vaccine formulations (K, L and M) as shown in Table 10 have been prepared and tested.

Vaccine K was formulated using the same procedure as the vaccines in the EXAMPLE 1 that have BLS peptides. The only difference for this vaccine is that this formulation contains both BLS peptides and whole inactivated antigens together.

Vaccines L and M were formulated using the same procedure as the vaccine in the EXAMPLE 1 that contains whole inactivated viral antigens.

(b) Animal Model:

23 Black Aberdeen Angus calves (male and female) between 6 and 10 months old, which have not been immunized with FMD vaccine, were recruited. All animals were tested by serology against FMDV whereby it was confirmed the absence of colostral antibody and/or vaccine related antibodies. The animals remained in the field throughout the entire clinical trial.

(c) Experimental Groups:

The animals were randomly divided into four experimental groups: Group 1 (n=10) was immunized with 2 mL of vaccine formulation K (Table 7, BLS-I_A2001+whole inactivated viral antigens strain O1 Campos); Group 2 (n=5) was immunized with 2 mL of vaccine formulation L (Table 7, whole inactivated viral antigens strain Argentina 2001); Group 3 (n=5) was immunized with 2 mL of vaccine formulation M (whole inactivated viral antigens strain O1 Campos). Finally, Group 4 (n=5) corresponds to the control group whose animals were not vaccinated.

(d) Vaccinations:

Experimental vaccines were administered only on day zero of the study. Table 11 shows the different schemes of vaccination.

(e) Bleedings:

Bleedings at 31 and 63 days post vaccination (DPV) were performed as shown in Table 11.

TABLE 11

Scheme of Vaccination

| Group number | Vaccine formulation | Description | Day 0 | Day 31 | Day 63 |
|---|---|---|---|---|---|
| 1 | K | BLS-I_A2001 + Viral O1-Campos | Vaccination | Bleeding (blood/serum) | Bleeding (serum) |
| 2 | L | Viral A2001 | Vaccination | Bleeding (blood/serum) | Bleeding (serum) |
| 3 | M | Viral O1-Campos | Vaccination | Bleeding (blood/serum) | Bleeding (serum) |
| 4 | Non vaccinated | Non vaccinated | — | Bleeding (blood/serum) | Bleeding (serum) |

TABLE 10

Formulation of vaccines

| Vaccines | K | L | M |
|---|---|---|---|
| Components | BLS-I_A2001[1] + Monovalent O1 Campos[3] | Monovalent A2001[2] | Monovalent O1 Campos[3] |
| Homogenizer | Ultraturrax | Silverson | Silverson |
| Type of emulsion | Single oil | Single oil | Single oil |
| Saponine | 3 mg/dose | 3 mg/dose | 3 mg/dose |
| Oil phase/Aqueous phase relation | 60:40 | 60:40 | 60:40 |
| Quantity of dose (2 ml/dose) | 6 | 2500 | 2500 |
| Aqueous phase volume (mL) | 4.8 | 2000 | 2000 |
| Oil phase volume (mL) | 7.2 | 3000 | 3000 |
| Antigenic Mass (ug/dose) | 1000[1] + 10[3] | 10 | 10 |
| Total vaccine volume (mL) | 12 | 5000 | 5000 |

Figure 11:
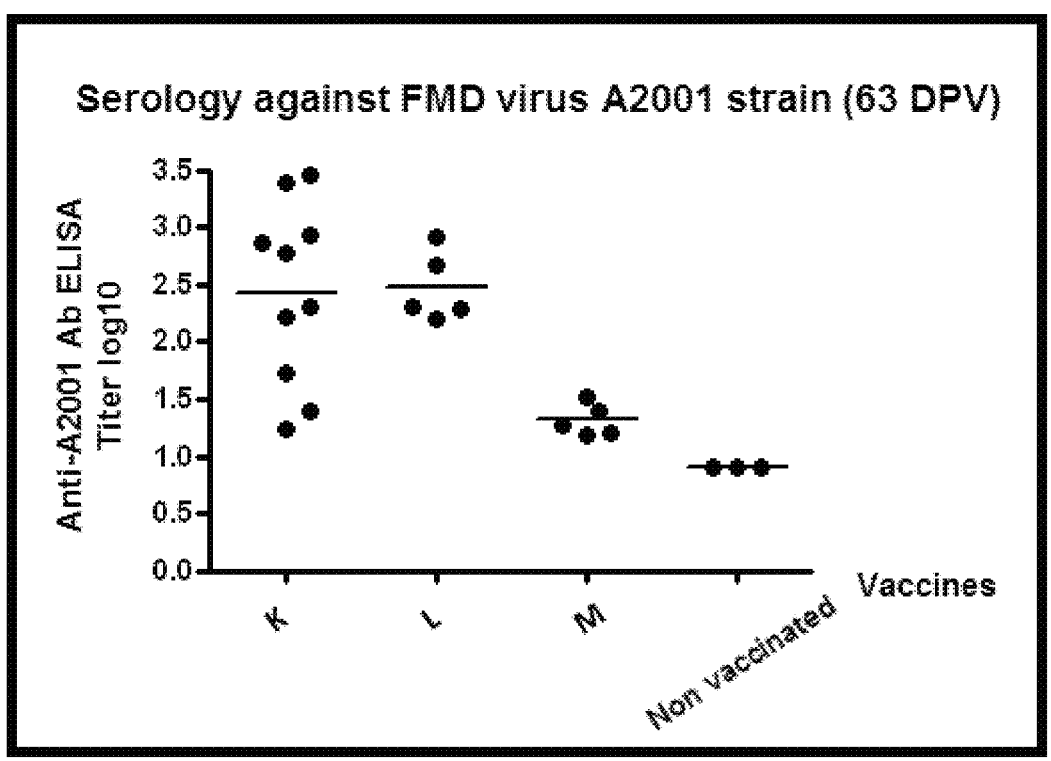

[1]BLS-I_A2001 (SEQ ID NO. 60): BLS protein expressing the immunogenic peptides I at the N-amino end; Peptide I (SEQ ID NO. 10): amino acids 136-156 of the VP1 protein of the FMDV strain A2001.
[2]Monovalent A2001: Inactivated FMDV serotype type A2001 whole virus
[3]Monovalent O1 Campos: Inactivated FMDV serotype type O1 Campos whole virus (f) Serology Against FMDV These analyses were performed by Liquid-Phase ELISA for A2001 specific antibodies. At 31 and 63 DPV, antibodies titers obtained in the groups immunized with monovalent viral vaccines were within expected values, with maximum values obtained in the case of homologous A2001 vaccine while minimum cross-reactive antibodies against A2001 were obtained in animals vaccinated with the strain O1 Campos. On the other hand, the vaccine formulation K (BLS-I_A2001+O1 Campos) was able to generate a great level of antibodies against A2001, as high as the positive control, showing once again a surprising and unforeseen synergistic effect between the recombinant BLS-peptides A2001 antigen and the whole virus O1 Campos antigen (FIGS. 10 and 11).

In conclusion, examples 5 and 7 have demonstrated that the combination of recombinant FMD antigen and whole inactivated FMDV is capable of triggering high antibody titers when both are applied together in the same vaccine or separately in different immunization strategies.

What is claimed is:

1. A vaccine formulation capable of cross-protection against one or more specific serotypes or strains of a Foot and Mouth Disease virus (FMDV), comprising whole inactivated viruses of a first serotype or strain of said Foot and Mouth Disease virus; and
   peptides, polypeptides or proteins as carriers or molecular adjuvants that are fused to:
   a) polynucleotides encoding peptides, polypeptides or proteins of said one or more specific serotypes or strains of said FMDV;
   b) synthetic peptides or polypeptides of said one or more specific serotypes or strains of said FMDV; or
   c) recombinant peptides, polypeptides or proteins of said one or more specific serotypes or strains of said FMDV.

2. The vaccine formulation of claim 1, wherein the formulation is capable of inducing protective immunity against one or more serotypes of FMDV selected from the group consisting of 0, A, C, Asia 1, SAT-1, SAT-2, and SAT-3.

3. The vaccine formulation of claim 1, wherein the polynucleotides of said FMDV comprise entire partial sequences selected from the grouping consisting of:
   a) polynucleotide sequences encoding one or more of FMDV capsid protein genes VP1, VP2, VP3 and VP4;

b) polynucleotide sequences encoding one or more of FMDV non-structural protein genes 2A, 2B, 2C, 2D, 3A, 3B, 3C and 3D; and
c) polynucleotide sequences encoding one or more of the peptides of SEQ ID NO. 1-55.

4. The vaccine formulation of claim 1, wherein said recombinant or synthetic viral peptides, polypeptides or proteins of said FMDV are recombinant or synthetic.

5. The vaccine formulation of claim 4, wherein said recombinant or synthetic viral peptides or polypeptides are linear or dendrimeric peptides.

6. The vaccine formulation of claim 1, wherein the whole inactivated viruses are serotype A.

7. The vaccine formulation of claim 1, wherein the carriers or molecular adjuvants are fused to polypeptides encoded by entire, partial or variant sequences of said FMDV, wherein said sequences are selected from the group consisting of:
  a) amino acid sequences of capsid protein VP1 of said FMDV;
  b) amino acid sequences of FMDV non-structural protein 3A of said FMDV;
  c) amino acid sequence having SEQ ID NO. 10; and
  d) amino acid sequences encoding peptides that are homologous or functional analogues to SEQ ID NO. 10.

8. The vaccine formulation of claim 7, wherein the carriers or molecular adjuvants are linear or dendrimeric.

9. The vaccine formulation of claim 7, wherein the carriers or molecular adjuvants comprises one or more of native amino acid sequence of *Brucella lumazine* synthase (BLS) protein, or its mutated variants having at least 85% identity to the sequences of *Brucella lumazine* synthase (BLS) protein.

10. A method of vaccinating a host susceptible to FMDV infection, comprising administrating to the host of the vaccine formulation of claim 1 to induce an immune response.

11. The method of claim 10, wherein the host is a cow, sheep, goat or swine.

12. The method of claim 10, wherein the induced immune response is humoral immune response or cellular immune response.

\* \* \* \* \*

UNITED STATES PATENT AND TRADEMARK OFFICE
CERTIFICATE OF CORRECTION

PATENT NO.         : 10,940,196 B2
APPLICATION NO.    : 16/092660
DATED              : March 9, 2021
INVENTOR(S)        : Rodolfo César Bellinzoni, Emmanuel Gérard Etienne Régulier and Ana Romo Page 1 of 1

It is certified that error appears in the above-identified patent and that said Letters Patent is hereby corrected as shown below:

In the Claims

In Column 60, Line 60 Claim 2, please replace "0, A, C" with --O, A, C--.

In Column 60, Lines 64-65 Claim 3, please replace "entire partial sequences" with --entire or partial sequences--.

In Column 61, Lines 20-21 Claim 7, please replace "FMDV non-structure protein 3A" with --non-structure protein 3A--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*